(12) United States Patent
Schuenzel et al.

(10) Patent No.: US 9,430,506 B2
(45) Date of Patent: Aug. 30, 2016

(54) ENTERPRISE MIGRATION PLANNING INFORMATION REPOSITORY

(71) Applicant: Accenture Global Services Limited, Dublin (IE)

(72) Inventors: Karl M. Schuenzel, Glenview, IL (US); Jonathan R. Harrison, Philadelphia, PA (US); Jeffrey P. Radack, Waterford, CT (US); Timothy P. Swope, Boston, MA (US); Caroline Pierri, Toronto (CA); Aimin Yin, North York (CA); Darcy Studer, Thornhill (CA); Zheng Wu, Markham (CA)

(73) Assignee: Accenture Global Services Limited, Dublin (IE)

( * ) Notice: Subject to any disclaimer, the term of this patent is extended or adjusted under 35 U.S.C. 154(b) by 321 days.

(21) Appl. No.: 13/779,297

(22) Filed: Feb. 27, 2013

(65) Prior Publication Data

US 2014/0172782 A1 Jun. 19, 2014

Related U.S. Application Data

(60) Provisional application No. 61/739,539, filed on Dec. 19, 2012.

(51) Int. Cl.
*G06F 17/30* (2006.01)
*G06F 7/00* (2006.01)
(Continued)

(52) U.S. Cl.
CPC .......... *G06F 17/303* (2013.01); *G06F 3/0605* (2013.01); *G06F 3/0607* (2013.01);
(Continued)

(58) Field of Classification Search
CPC .......... G06F 17/303; G06F 17/30286; G06F 17/30067; G06F 17/30575; G06F 3/0647; G06F 3/067; G06Q 10/10
USPC ........................................ 707/609
See application file for complete search history.

(56) References Cited

U.S. PATENT DOCUMENTS 6,151,608 A * 11/2000 Abrams ............... G06F 17/303
707/679
2004/0194055 A1* 9/2004 Galloway .............. G06F 8/76
717/101
(Continued)

FOREIGN PATENT DOCUMENTS

EP 1857946 A2 11/2007
EP 1857946 A3 12/2007

OTHER PUBLICATIONS

Christopher Clark et al., "Live Migration of Virtual Machines," dated May 2, 2005, pp. 273-286, USINEX, 2nd Symposium on Networking Systems Design & Implementation, Boston, USA.

(Continued)

*Primary Examiner* — Usmaan Saeed
*Assistant Examiner* — Raquel Perez-Arroyo
(74) *Attorney, Agent, or Firm* — Brinks Gilson & Lione

(57) ABSTRACT

A data migration tool is disclosed for allowing a data migration project to be more efficient to execute from the client standpoint. The data migration tool is able to accomplish this by offering an efficient process for receiving the client's data migration requirements and generating a migration schedule based on the client's data migration requirements. The client's data migration requirements may identify one or more migration rules relating the data to be migrated as well as the client's scheduling conflicts. Based on the data migration requirements, the data migration tool can generate a data migration schedule. The data migration schedule may include a sequence in which data entities are migrated, as well as provide migration activities that describe the specific instructions for migrating a data entity.

22 Claims, 15 Drawing Sheets

(51) Int. Cl.
*G06F 9/445* (2006.01)
*G06F 3/06* (2006.01)
*G06Q 10/10* (2012.01)
*G06Q 50/22* (2012.01)
*H04L 29/08* (2006.01)

(52) U.S. Cl.
CPC ............ *G06F 3/067* (2013.01); *G06F 3/0647* (2013.01); *G06F 3/0653* (2013.01); *G06F 8/61* (2013.01); *G06F 9/44505* (2013.01); *G06Q 10/10* (2013.01); *G06Q 50/22* (2013.01); *H04L 67/325* (2013.01); *H04L 67/06* (2013.01); *H04L 67/34* (2013.01)

(56) References Cited

U.S. PATENT DOCUMENTS

| | | |
|---|---|---|
| 2006/0129771 A1 | 6/2006 | Dasgupta et al. |
| 2007/0245110 A1 | 10/2007 | Shibayama et al. |
| 2008/0201542 A1 | 8/2008 | Maruyama et al. |
| 2008/0255895 A1 | 10/2008 | Rajamony et al. |
| 2009/0043822 A1 | 2/2009 | Sarkar et al. |
| 2010/0325378 A1* | 12/2010 | Maruyama ............ G06F 3/0607 711/162 |
| 2012/0131567 A1* | 5/2012 | Barros .................. G06F 9/5088 717/170 |
| 2012/0151061 A1* | 6/2012 | Bartfai-Walcott .... G06F 9/4856 709/226 |

OTHER PUBLICATIONS

Steven Hand, "Systems Virtualization," dated Jul. 11, 2010, pp. 40-50, University of Cambridge / HIPEAC—ACACES Sixth International Summer School on Advanced Computer Architecture and Compilation for High-Performance and Embedded Systems, Terrassa (Barcelona), Spain.

Extended European Search Report, dated Mar. 7, 2014, pp. 1-12, Issued in European Application No. 13005904, The Hague, The Netherlands.

Australian Examination Report No. 1, dated Jul. 11, 2014, pp. 1-2, Australia Patent Application No. 2013273685, issued by IP Australia, Woden, ACT 2606, Australia.

* cited by examiner

FIG. 7

ENTERPRISE MIGRATION PLANNING INFORMATION REPOSITORY

BACKGROUND OF THE INVENTION

It is often desirable, or even necessary, to migrate data from one data storage system to another. For instance, a company may need to migrate their data from an older, out of date, storage system to a newer, more modern and secure, data system. In another scenario, a parent company may acquire another company, in which case the data that is stored on the storage servers of the company that has been bought out need to be migrated to the parent company's data storage system. And in another scenario, patient data may be migrated from the data storage systems from many different hospitals to a central data storage system for consolidating the patient data.

In any scenario, data migration can be a major project as it may require the transfer of large amounts of data from one data storage system to another data storage system. Migrating large amounts of data may also require a significant investment of human resource talent to plan and oversee the data migration project. However, investing a significant portion of a company's human resource talent into a large data migration project has many pitfalls.

For one, the significant drain of human resource talent may be overly expensive for the company to absorb. In addition, exposing the data migration project to so many human workers leaves the data migration project vulnerable to human errors.

Therefore, there is a need to introduce a more efficient data migration process that is able to utilize computing resources to take on a greater role in planning, validating and executing a data migration project.

SUMMARY OF THE INVENTION

According to an aspect of the present invention, a method of implementing a data migration project for migrating a set of application data from a source data storage system to a destination data storage system is disclosed, the method comprising: receiving, at a controller, a set of data migration rules; receiving, at the controller, a set of scheduling consideration; comparing the set of data migration rules against the set of scheduling considerations; determining whether conflicts arise between the set of migration rules and the set of scheduling considerations based on the comparison, and generating a migration schedule for migrating the set of application data based on the determination.

According to another aspect of the present invention, a workstation for implementing a data migration project for migrating a set of application data from a source data storage system to a destination data storage system is disclosed, the workstation comprising: a memory configured to store a set of data migration rules and a set of scheduling considerations; and a controller configured to: compare the set of data migration rules against the set of scheduling considerations; determine whether conflicts arise between the set of migration rules and the set of scheduling considerations based on the comparison, and generate a migration schedule for migrating the set of application data based on the determination.

According to another aspect of the present invention, a computer readable memory storing a set of instructions for implementing a data migration project for migrating a set of application data from a source data storage system to a destination data storage system is disclosed, the set of instructions being executed by a processor to: store a set of data migration rules and a set of scheduling considerations; compare the set of data migration rules against the set of scheduling considerations; determine whether conflicts arise between the set of migration rules and the set of scheduling considerations based on the comparison, and generate a migration schedule for migrating the set of application data based on the determination.

BRIEF DESCRIPTION OF THE DRAWINGS

The present invention may be better understood with reference to the following drawings and description. Non-limiting and non-exhaustive descriptions are described with reference to the following drawings. The components in the figures are not necessarily to scale, emphasis instead being placed upon illustrating principles. In the figures, like referenced numerals may refer to like parts throughout the different figures unless otherwise specified.

FIG. 7 illustrates a graphical representation of a migration schedule, according to the present invention;

DETAILED DESCRIPTION

Figure 1:
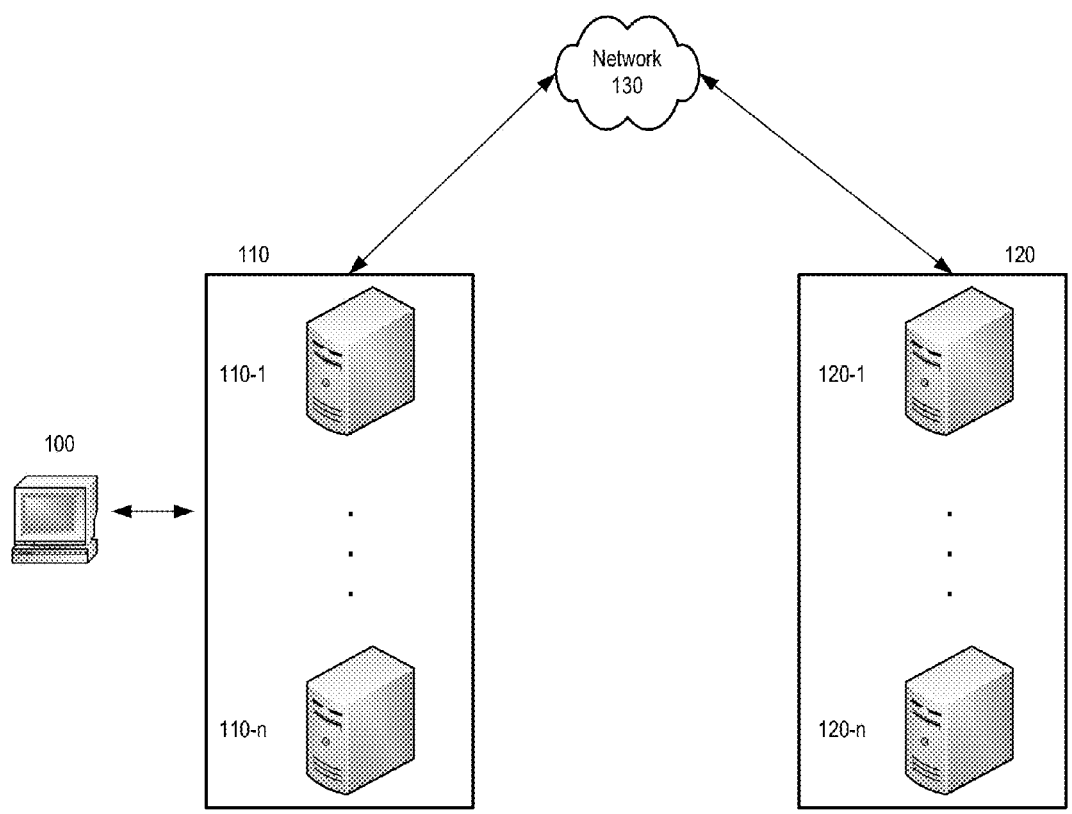
FIG. 1 illustrates an exemplary system including the various components for achieving the processes according to the present invention.

The present invention as described herein may be embodied in a number of different forms. Not all of the depicted components may be required, however, and some implementations may include additional, different, or fewer components from those expressly described in this disclosure. Variations in the arrangement and type of the components may be made without departing from the spirit or scope of the claims as set forth herein.

The illustrations described herein are intended to provide a general understanding of the structure of various embodiments. The illustrations are not intended to serve as a complete description of all of the elements and features of apparatuses, processors, and systems that utilize the structures or methods described herein. Other embodiments may be apparent to those of skill in the art upon reviewing the disclosure. Other embodiments can be utilized and derived from the disclosure, such that structural and logical substitutions and changes can be made without departing from the scope of the disclosure. Additionally, the illustrations are merely representational and cannot be drawn to scale. Certain proportions within the illustrations may be exaggerated, while other proportions may be minimized. Accordingly, the disclosure and the figures are to be regarded as illustrative rather than restrictive.

Large scale data migration projects may pose a number of difficulties. Some examples of difficulties that may arise during the planning and execution of a large scale data migration project includes, but is not limited to, planning large scale and complex data migration across numerous data sources and data destinations, complex multi-data source application and infrastructure dependencies and relationships, dynamic data migration configuration and inventory control, multi-department and multi-skilled resource management within a client (e.g., human resource talent within a company), complex and fluid migration script tracking and management, difficult and loose migration wave execution command and control, lack of real-time reporting and data migration visibility, and lack of sole source master data management. The present disclosure seeks to provide a system, apparatus and/or method for addressing such difficulties that may arise during a data migration project.

Some of the benefits provided by the automated processes and tools described in this disclosure include, but are not limited to, providing a centralized management point from which to plan and manage a data migration inventory, relational and single source data migration inventory, documentation of mapping migrating applications to their corresponding infrastructure components, integrated migration activity tracking and resource management, extensive command and control of the data migration process, auditing capabilities of each wave of data during the data migration, improved speed to market and reduced data migration execution costs, and off premise, web accessible security controlled access.

FIG. 1 illustrates an exemplary data migration system 1 for executing a data migration project according to the tools and methods described herein. The data migration system 1 is comprised of a workstation 100, source data storage system 110, a network 130, and destination data storage system 120. The data migration project generally looks to migrate data that is stored on a client's source data storage system 110, to the destination data storage system 120.

The source data storage system 110 may be comprised of one or more source data servers 110-1 to 110-$n$. Each source data server 110-1 to 110-$n$ that comprises the source data storage system 110 includes at least a controller and memory unit for storing one or more applications and other data that will be the subject of the data migration project. The memory unit may be a random-access memory, read-only memory, programmable memory, hard disk drive or any other type of volatile or non-volatile memory or storage device.

Figure 2:
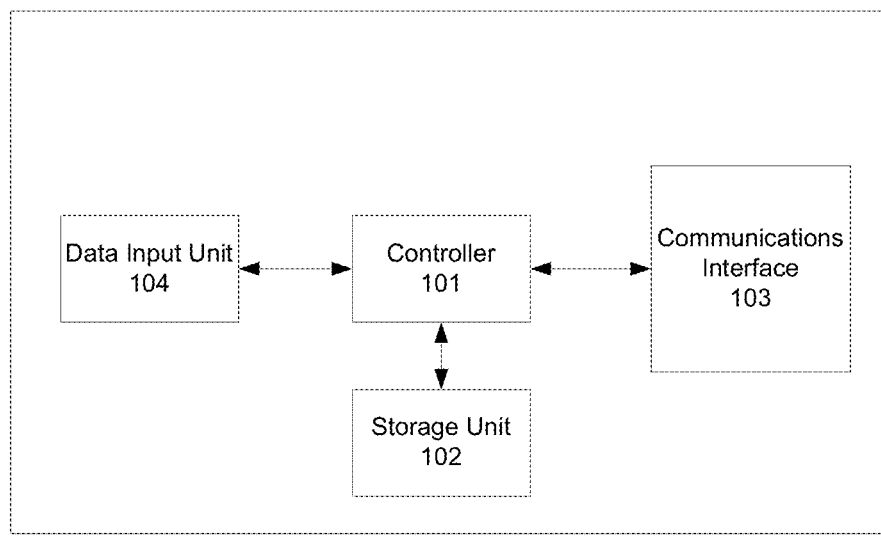
FIG. 2 illustrates a block diagram of a communication device, according to the present invention.

Coupled to the source data storage system 110 is a workstation 100. The workstation 100 may be a computer workstation, smartphone, server, laptop, tablet, personal computer or any other like computing device. FIG. 2 illustrates a block diagram for an exemplary workstation 100 included in the data migration system 1.

The workstation 100 is illustrated in FIG. 2 as being comprised of a controller 101, storage unit 102, communications interface 103 and a data input unit 104. Although the workstation 100 is illustrated in FIG. 2 as being comprised of the above described components, the workstation 100 is not limited to such configuration, and may be comprised of fewer or more components in other embodiments. For example, the workstation 100 may also include a display unit.

It is noted that although FIG. 1 illustrates a single workstation 100 being coupled to the source data storage system 110, it is contemplated that one or more workstations 100 may be coupled to the source data storage system 110 for running a data migration tool that will be managing the data migration project disclosed herein.

The storage unit 102 may, for example, be a random-access memory, read-only memory, programmable memory, hard disk drive or any other type of volatile or non-volatile memory or storage device or computer readable memory. The storage unit 102 may store a listing of a set of instructions that may be executed by the controller 101 to cause the workstation 100 to perform any one or more of the processes and methods disclosed herein. For example, the set of instructions stored in the storage unit 102 may correspond to program instructions for executing the data migration tool that will be described throughout this disclosure as performing any one or more of the processes and methods disclosed herein.

The workstation 100 may be coupled to the source data storage system 110 via a wired or wireless connection provided by the communications interface 103. In this way, the communications interface 103 provides the workstation 100 the capability to communicate with the source data storage system 110 either directly (in either a wired or wireless connection) or via the network 130.

In the embodiments where the workstation 100 is coupled to the source data storage system 110 in a wired connection, the communications interface 103 may enable communication via any number of communication standards such, but not limited to, IEEE 1394, USB, USB 2.0, USB 3.0, Ethernet, and/or other like wired connection standards.

In the embodiments where the workstation 100 is a mobile device, the communications interface 103 may enable communication via any number of wireless communication standards, such as, but not limited to WiFi, 802.11, 802.17, 802.20, WiMax, 802.15.4, cellular telephone standards, data network standards and/or other communication standards for interfacing via the network 130. The communications interface 103 on the workstation 100 may also enable wireless communication directly with the source data storage system 110 according to the Bluetooth, near field communication (NFC), radio frequency (RF) and/or other similar wireless data communication standards.

The data input unit 105 of the workstation 100 may, for example, be a touchscreen, keyboard, touch pad, mouse, voice input unit, visual recognition unit or other like device for receiving a user's input into the workstation 100.

The controller 101 may, for example, be a computing processor for controlling the various components that comprise the workstation 100. The controller 101 may also execute the executable instructions that comprise the data migration tool stored on the storage unit 103 for implementing the methods and processes disclosed herein.

The network 130 illustrated in FIG. 1 may be a cellular network, including standards-based networks (e.g., 2G, 3G, Universal Mobile Telecommunications System (UMTS), GSM® Association, Long Term Evolution (LTE)™, or more), WiMAX, Bluetooth, WiFi (including 802.11 a/b/g/n/ac or others), WiGig, Global Positioning System (GPS) networks, and others available at the time of the filing of this application or that may be developed in the future. Further, the network may be a public network, such as the Internet, a private network, such as an intranet, or combinations thereof, and may utilize a variety of networking protocols now available or later developed including, but not limited to TCP/IP based networking protocols.

FIG. 1 also illustrates the destination data storage system 120. The destination storage system 120 is comprised of one or more destination data servers 120-1 to 120-n. Each destination data server 120-1 to 120-n that comprises the destination data storage system 120 includes a memory unit for storing the one or more applications and other data that are received from the source data storage system 110 according to the data migration project. The memory unit may be a random-access memory, read-only memory, programmable memory, hard disk drive or any other type of volatile or non-volatile memory or storage device.

Figure 3:
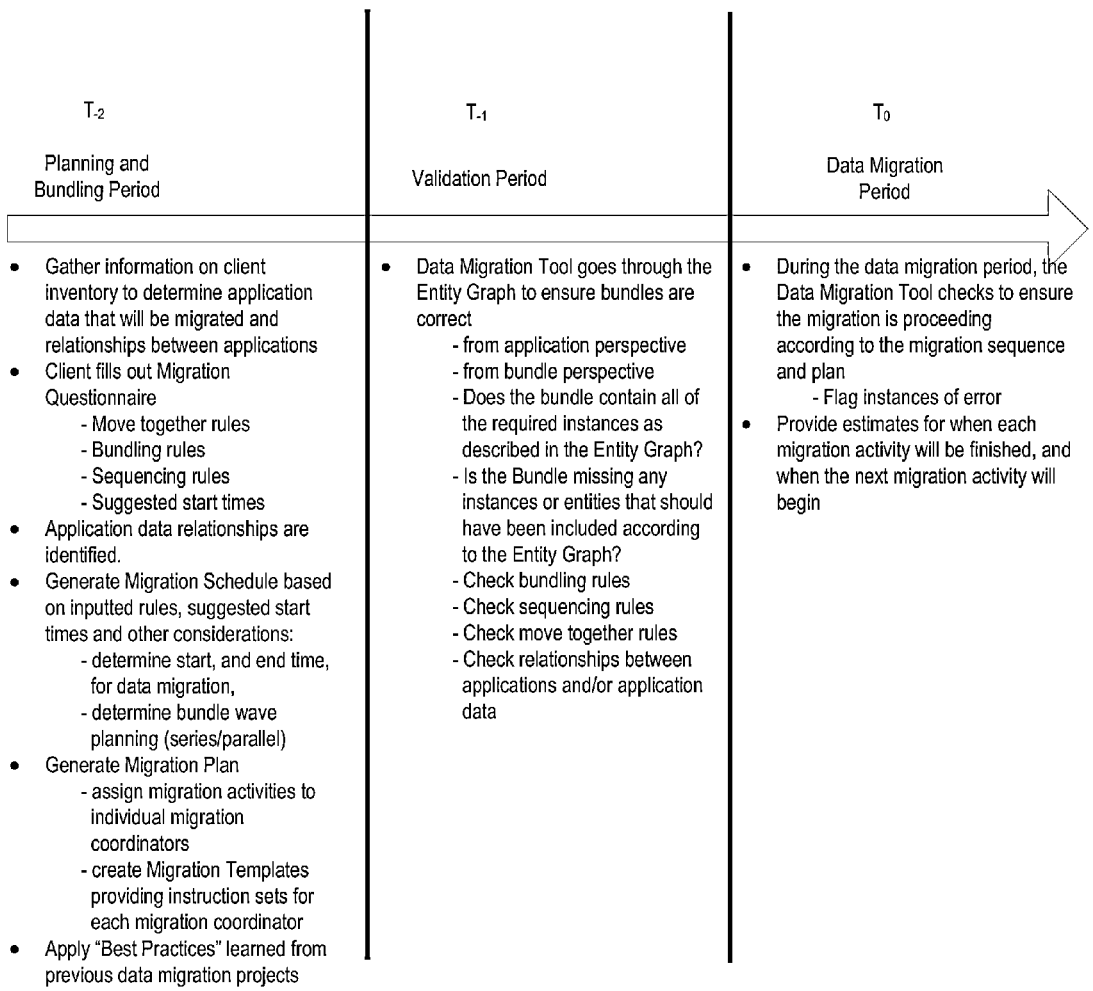
FIG. 3 illustrates an exemplary time line for executing the various processes and features according to the present invention.
Figure 4:
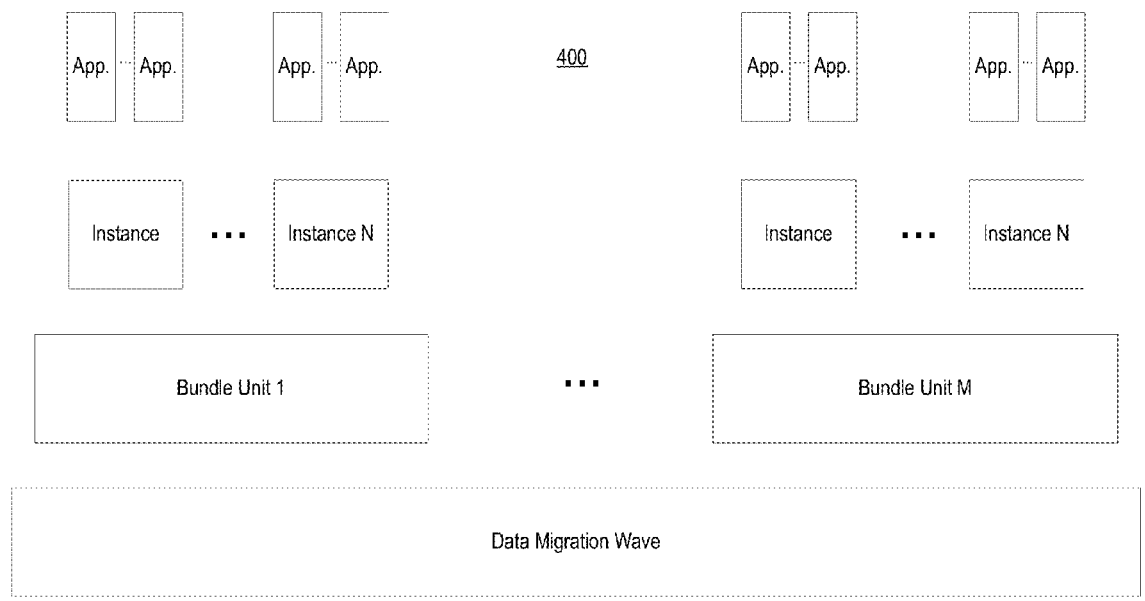
FIG. 4 illustrates the composition of an exemplary data migration wave.

FIG. 3 illustrates an exemplary timeline of events that may occur during the implementation of a data migration project for migrating a client's data from the source data storage system 110 to the destination data storage system 120. In general, the data migration project will migrate the client's data in a series of one or more data migration waves. FIG. 4 illustrates the composition of an exemplary data migration wave 400. As illustrated in FIG. 4, a data migration wave 400 may be comprised of M bundle units, and a bundle unit may be comprised of N instances and/or other application data. An instance may describe application data and/or other data that is stored on a specific client server.

The data migration project is illustrated in FIG. 3 as being partitioned into three exemplary time periods: $T_{-2}$, $T_{-1}$, and $T_0$. The three time periods have been labeled as such to identify $T_0$ as the time period during which the data migration is being executed, while $T_{-2}$ and $T_{-1}$ are two earlier time periods during which various preparatory measures are executed. Further detail on the individual times $T_{-2}$, $T_{-1}$, and $T_0$ are provided below.

The time period labeled as $T_{-2}$ may be considered to be a planning and data bundling period. During the $T_{-2}$ time period, an inventory of the client's data to be migrated may be taken. The client's data may be comprised of applications, application data and other data for supporting the applications. The client's data inventory may be taken in order to identify shared infrastructure relationships between the client's application data. For example, the inventory process may identify that a number of applications share a common active directory infrastructure. The inventory process may also identify that a number of applications share a common firewall infrastructure. Such applications that share a common infrastructure may be bundled together and/or scheduled to be migrated within a same data migration wave. Identifying applications that share a common infrastructure as needing to be bundled together and/or scheduled to be migrated within a same data migration wave are examples of a bundling rule and move together rule, respectively.

During the inventory process, the applications may also be subjected to an initial classification structure. For example, applications may be classified as having a high complexity, medium complexity, or low complexity. The level of complexity may be referenced later during a bundling process, where applications sharing a same level of complexity may be bundled together and/or scheduled to be migrated within a same data migration wave. Identifying a class of applications as needing to be bundled together and/or scheduled to be migrated within a same data migration wave are examples of a bundling rule and move together rule, respectively.

The results from the inventory process may then be input into the data migration tool according to the present invention. By providing the client's inventory information into the data migration tool, the data migration tool may obtain a better understanding of the scope and complexity of the client's desired data migration project.

Also during the $T_{-2}$ time period, the client may be given a migration questionnaire to fill out. As part of the migration questionnaire, the client may be asked to define application to instance relationships. For example, an instance may represent a physical server such that an application to instance relationship identifies which applications are stored on a common server (e.g., instance). Based on the application to instance relationship, applications that are stored on a common instance may be grouped into a common bundle unit as a bundling rule. In addition or alternatively, later during the scheduling process, groupings may be specified to indicate which instances need to move at the same time from the perspective of the current application. This is another example of a move together rule.

The migration questionnaire may also ask the client to define applications that are known to share services, such as software services. For example, applications that are running on a common shared database server may be known to share resources. In such cases, the client may identify whether the applications that are known to share services should be bundled together and/or migrated together within a common data migration wave. These are more examples of a bundling rule and a move together rule, respectively.

The migration questionnaire may also ask the client to define applications that interface, interact, or rely on each other. In such cases, the client may identify whether the applications that are known to interface, interact, or rely on each other should be bundled together and/or migrated together within a common data migration wave. These are more examples of a bundling rule and a move together rule, respectively.

A portion of the migration questionnaire may additionally ask the client to input one or more bundling rules for grouping applications and other data stored on the client's data servers into individual bundle units. A bundle unit is considered to be the minimum set of data configured to move together during a data migration wave. One example of a bundle rule that may be input by the client is to have all applications and/or other data that are stored on a common data server (e.g., same instance) to be bundled into a common bundle unit. Another example of a bundle rule may focus on common shared services, such that one or more applications and/or other related data that are related to a common shared service may be bundled into a common bundle unit. Another example of a bundle rule may focus on related applications, such that one or more applications and/or other related data that interface, interact, or rely on each other may be bundled into a common bundle unit. The one or more applications and/or other related data may be stored on a common data server, or may be stored across multiple data servers.

Additionally, the client may identify certain instances, applications, bundle units, or other data units as needing to be migrated together within a common data migration wave as another example of a move together rule. For example, under the rules provided above, an application may be identified as belonging to more than one bundle unit. In such a case, all of the bundle units that are identified as related to the specific application may be grouped into a common data migration wave.

In addition to the bundling rules that are input by the client into the migration questionnaire, previous bundling rules that were implemented during a previous data migration project may be re-implemented for the current data migration project. A previous bundling rule that is highlighted for re-implementation may have been recognized as providing an efficient method for bundling data during the previous data migration project. The previous bundling rule may have been recognized from a previous data migration project executed by the current client. In addition or alternatively, the previous bundling rule may have been recognized from another data migration project executed by the same, or different, client but one that still utilized the same data migration tool. In this case, the data migration tool may have access to a database of previous bundling rules that have been implemented across one or more different clients that are highlighted for various reasons of offering a beneficial result during a previous data migration project. The database of previous bundling rules that is accessible by the data migration tool may be part of a larger "best practices" database that includes highlighted information from previous data migration projects executed by the current client and/or other clients that have utilized the data migration tool. Details on other information that may be included in such a best practices database are provided herein.

After inputting the bundling rules, the client may optionally organize the client's inventory of data into the bundle units defined by the bundling and move together rules. Alternatively, the client may operate the data migration tool to assign the applications and data stored in each source data server into their appropriate bundle units according to the bundling rules and move together rules described above. In this way, the data migration tool may parse the applications and other data stored on the client's source data servers and organize the applications and other data into their respective bundle units according to the bundling rules. In some embodiments, the bundling units may be assigned according to a mix of manual input by the client, and automated assignment by the data migration tool referencing the bundling rules.

In addition to the bundling and move together rules, the client may identify one or more sequencing rules for input into the data migration tool. A sequencing rule may identify predecessor and successor rules for migrating applications, application data, instances, bundle units and/or other units of data for the data migration project. For exemplary purposes only, an application, application data, instance, bundle unit and/or other units of data for the data migration project may be referred to as an entity throughout this disclosure. A predecessor rule may identify one or more entities that must be migrated before one or more other entities. A successor rule may identify one or more entities that must be migrated after one or more other entities. Similarly, the client may input sequencing rules with regards to data migration waves. So a predecessor rule may identify one or more data migration waves that must be migrated before one or more other identified data migration waves. And a successor rule may identify one or more data migration waves that must be migrated after one or more other identified data migration waves.

In addition to the rules described above, the client may also input scheduling considerations that identify the client's preferred start and/or end times for one or more migration event into the data migration tool. For example, the client may input a preferred start and end time for the overall data migration project. The client may also input a preferred start and/or end time for one or more activities that are required to migrate a specific entity. Further description of the activities required to migrate a specific entity will be provided below. In addition, the scheduling considerations may include the client's scheduling information and conflicts that identify times during which the client is available, and unavailable, to accomplish the activities required to migrate entities and to generally monitor the data migration.

Now with all of the rules, preferred start time information and/or the client's scheduling considerations input into the data migration tool, the client may initiate the data migration tool to generate a migration schedule. The data migration tool may then reference one or more of the rules and/or client scheduling considerations to generate the migration schedule of the data migration project.

The data migration tool may compare one or more of the rules input by the client against the client's scheduling considerations and identify any conflicts that may arise. If all of the rules input by the client can be satisfied without interfering with the client's scheduling considerations, then the data migration tool may generate the migration schedule to implement the client inputted rules and the client's scheduling considerations. However, if conflicts are detected between the inputted rules and the client's scheduling considerations, then the data migration schedule may be generated to implement as many of the rules as possible while maintaining the client's scheduling considerations. Alternatively, the data migration tool may generate the migration schedule to implement the inputted rules while implementing as many of the client's scheduling considerations as possible. Alternatively, the data migration tool may generate the migration schedule to implement one or more, but not all, of the rules while also implementing one or more, but not all, of the client's scheduling considerations. For example, the client may flag a specific rule or scheduling consideration to have precedence, in which case the specific rule or scheduling consideration will have to be implemented in the generated migration schedule over the implementation of other rules or scheduling considerations.

The migration schedule generated by the data migration tool may identify a start and finish time for the data migration portion of the data migration project. For instance, the start time for the data migration portion may coincide with the start time for the $T_0$ time period, and the finish time for the data migration portion may coincide with the finish time for the $T_0$ time period. Consequently, the duration of the data migration may also be calculated from the difference of the start and finish times.

In generating the migration schedule, the data migration tool will look to uphold the move together, bundling, and sequencing rules against the client's scheduling information. In some embodiments all of the client's rules may be upheld to fit within the client's scheduling information. In other embodiments, one or more, but not all, of the rules may be upheld.

Figure 5:
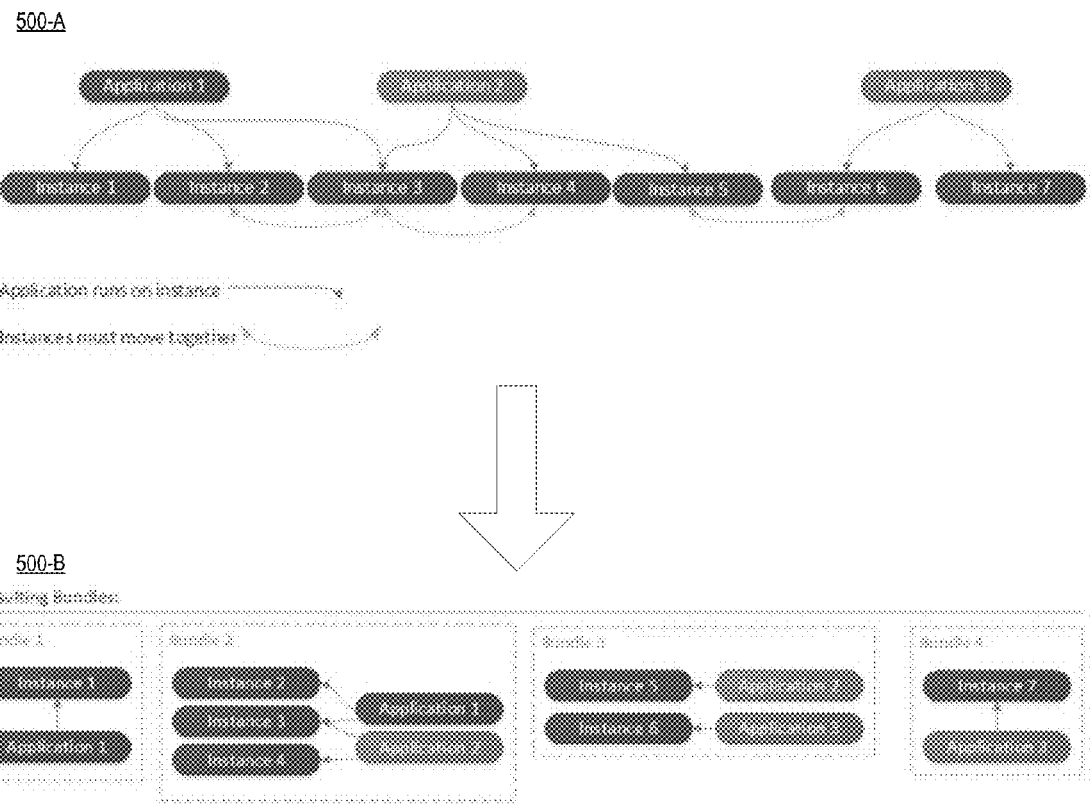
FIG. 5 illustrates a relationship tree for grouping entities into bundle units, according to the present invention.

For example, FIG. 5 illustrates a relationship tree 500-A that maps a move together rule for bundling entities. Specifically, the move together rule being implemented in the relationship tree 500-A looks to bundle Instance 2, Instance 3 and Instance 4 together, as well as the applications running on each of the aforementioned instances. The move together rule also looks to bundle Instance 5 and Instance 6 together, as well as the applications running on each of the aforementioned instances. FIG. 5 illustrates that Application 1 is running on Instance 1, Instance 2 and Instance 3. Application 2 is illustrated as running on Instance 3, Instance 4 and Instance 5. Application 3 is illustrated as running on Instance 6 and Instance 7. By implementing the move together rule, the resulting bundling map 500-B illustrates that Bundle 1 is comprised of Instance 1 as well as Application 1, Bundle 2 is comprised of Instances 2, 3, 4 as well as Applications 1 and 2, Bundle 3 is comprised of Instances 5, 6 as well as Applications 2 and 3, and Bundle 4 is comprised of Instance 7 as well as Application 3.

As another example, the data migration tool may have generated the migration schedule to have implemented one or more of the received rules to bundle one or more entities sharing a common infrastructure into a common bundle unit, as identified by the client input.

The data migration tool may also generate the migration schedule to have implemented one or more of the received rules to bundle one or more entities that belong to a same classification into a common bundle unit, as identified by the client input.

The data migration tool may also generate the migration schedule to have implemented one or more of the received rules to bundle one or more entities that are related to a common instance into a common bundle unit. For example, entities that are stored on a common instance server may be grouped into a common bundle unit, as identified by the client input.

The data migration tool may also generate the migration schedule to have implemented one or more of the received rules to bundle one or more entities that share a common service into a common bundle unit. For example, entities that are identified as sharing a same software service, such as from being executed for storage on a shared database server, may be grouped into a common bundle unit, as identified by the client input.

The data migration tool may also generate the migration schedule to have implemented one or more of the received rules to bundle one or more entities that are identified as being known to interface, interact, or rely on each other into a common bundle unit, as identified by the client input.

The data migration tool may also generate the migration schedule to have implemented one or more of the received rules to organize the bundle units into one or more data migration waves. Each data migration wave in the migration schedule may include one or more bundle units. The data migration tool may further sequence each data migration wave to implement one or more of the received sequencing rules, as identified by the client input.

For example, the data migration tool may generate the migration schedule to assign bundle units BU1, BU2 and BU3 to a first data migration wave W1. Similarly, bundle units BU4 and BU5 may be assigned to a second data migration wave W2. And a single bundle unit B6 may be assigned to a third data migration wave W3. Given this scenario, the migration schedule may implement one or more sequencing rules that outline specific predecessor and successor relationships between individual data migration waves. For example, the sequencing rules may state W1 is to be migrated before W2, and W2 is to be migrated before W3. In other words, the sequencing rules may state that certain data migration waves are to precede or follow certain other data migration waves. Given these sequencing rules, the migration schedule may identify that the data migration project is to migrate the three data migration waves in the following sequence: W1, then W2, and finally W3. In this way, the sequencing rules may be implemented as being dependent on a sequential migration relationship between data migration waves. The sequencing rules, for example, may be inputted by the client or be part of a database (e.g., best practices database).

In addition or alternatively, the migration schedule may implement one or more sequencing rules that outline specific predecessor and successor relationships between individual bundle units. For example, the implemented sequencing rules may state BU1 is to be migrated before BU2, and BU2 is to be migrated before BU3. In other words, the sequencing rules may state that certain bundle units are to precede or follow certain other bundle units. Given these exemplary sequencing rules, the migration schedule may identify that the data migration is to migrate the bundle units in the following sequence: migrate the data migration wave including BU1, then the data migration wave including BU2, and finally the data migration unit that includes BU3. In this way, the sequencing rules may be implemented as being dependent on a sequential migration relationship between bundle units. The sequencing rules, for example, may be inputted by the client or be part of a database (e.g., best practices database).

In addition or alternatively, the migration schedule may implement one or more sequencing rules that outline specific predecessor and successor relationships between individual entities within a common bundle unit. For example, the implemented sequencing rules may state that Application 1 is to be migrated before Application 2, and Application 2 is to be migrated before Application 3. In other words, the sequencing rules may state that certain applications within a bundle unit are to precede or follow certain other applications within the same common bundle unit. Given these exemplary sequencing rules, the migration schedule may identify that the data migration is to migrate the applications in the following sequence: migrate Application 1 first, migrate Application 2 after Application 1, and migrate Application 3 after Application 2. In this way, the sequencing rules may be implemented as being dependent on a sequential migration relationship between applications (or other types of entities) within a common bundle unit. The sequencing rules, for example, may be inputted by the client or be part of a database (e.g., best practices database).

In addition to generating the migration schedule to implement one or more of the rules described above, the data migration tool may identify stray entities and other data during the generation of the migration schedule. Stray entities are those entities that may not have been accounted for in the client's migration questionnaire. For example, stray entities may not belong to any particular bundle unit due to being unaccounted for or due to being added to the data migration project after the rules and relationships were initially implemented in the migration schedule. In such cases where stray entities may be found, the data migration tool will allocate the identified stray entities into bundle units. If the data migration tool can identify characteristics of the stray entities that relates it to any one or more of the bundle units, the data migration tool may allocate the stray entities to those related bundle units. For example, if a stray entity is identified by the data migration tool as having characteristics that apply it under one of the rules or relationships described above, the stray entity may be included with the corresponding bundle unit. Otherwise, the data migration tool may allocate stray entities to bundle units in the order of bundle units containing the least amount of data according to memory size.

According to some embodiments, the migration schedule may optionally be generated to identify the destination data storage system for migrating one or more of the bundle units of application data in the data migration project. In some embodiments, the destination data storage system may be input by the client. In other embodiments, the data migration tool may reference a set of destination rules for determining a data migration destination for a particular bundle unit (e.g., the destination rules may be included in the best practices database). The destinations rules may identify a destination data storage system, and in some cases more specifically a destination data server, based on characteristics of the bundle unit and/or the destination data storage system and destination data server. For example, the destination rules may indicate that bundle units that include application data related to highly sensitive information are to be migrated to destination data servers that can offer secure storage of the application data (e.g., application data may be encrypted upon storage on the secure data server). In this way, the data migration tool may reference the destination rule(s), determine characteristics of the bundle units, and locate one or more destination data storage systems (or more specifically destination data servers) for migrating the bundle units that satisfy the destination rule(s).

The migration schedule may also be generated to define one or more specific activities required to migrate an entity, and then assign the one or more specific activities for migrating the entity to an operator. For example, the migration schedule may assign each of the defined migration activities to a client side migration coordinator. The migration coordinator may be an employee of the client, a program being executed on the workstation 100 that is dedicated to accomplishing the assigned migration activities, or a combination of the two. The migration coordinator will be responsible for managing the migration activities that are assigned to the migration coordinator.

In order to assist the migration coordinator to successfully accomplish their migration activity task, the migration schedule may also include one or more migration scripts for each entity within a generated bundle unit. Each script may describe a migration activity for migrating a corresponding entity, and further provide specific instructions for accomplishing the migration activity and how each migration activity is to be managed and completed. These migration scripts may be inputted to the data migration tool by the client, and later made available to migration coordinators as a set of instructions detailing the migration coordinators role in managing migration activities in the data migration project.

Figure 6A:
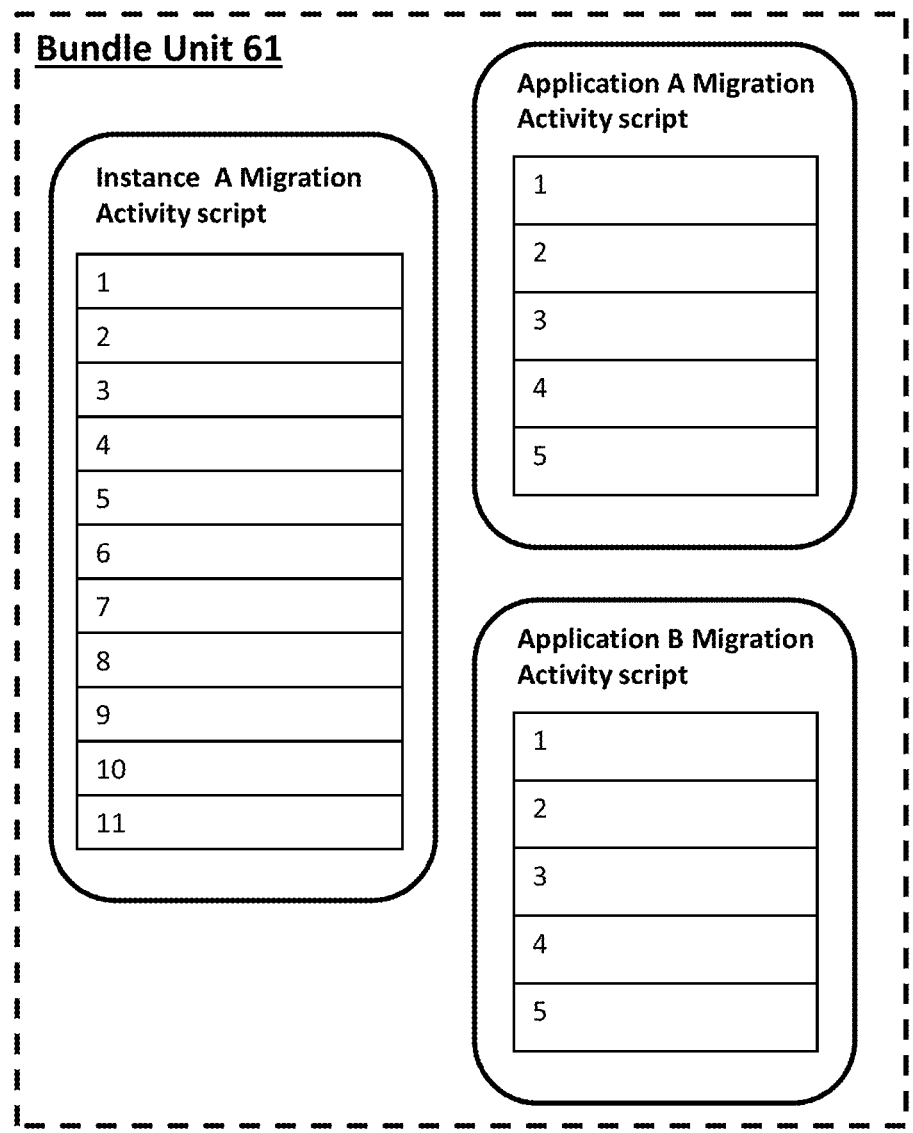
FIG. 6A illustrates an exemplary bundle unit including corresponding migration activity scripts, according to the present invention.

For example, FIG. 6A illustrates Bundle Unit 61 including the following entities: Instance A, Application A, and Application B. Each entity is shown to have its own set of migration activities for migrating the entity, provided in their respective migration activity scripts. Instance A is illustrated as having a migration activity script comprised of ten (11) migration activities. Application A is illustrated as having a migration activity script comprised of five (5) migration activities. And Application B is illustrated as having a migration activity script comprised of five (5) migration activities. The specific migration activities are not provided in detail as FIG. 6A is provided for exemplary purposes only. The actual migration of Instance A may require a fewer, or greater, number of migration activities than illustrated in FIG. 6A. The actual migration of Application A may require a fewer, or greater, number of migration activities than illustrated in FIG. 6A. The actual migration of Application B may require a fewer, or greater, number of migration activities than illustrated in FIG. 6A.

Figure 6B:
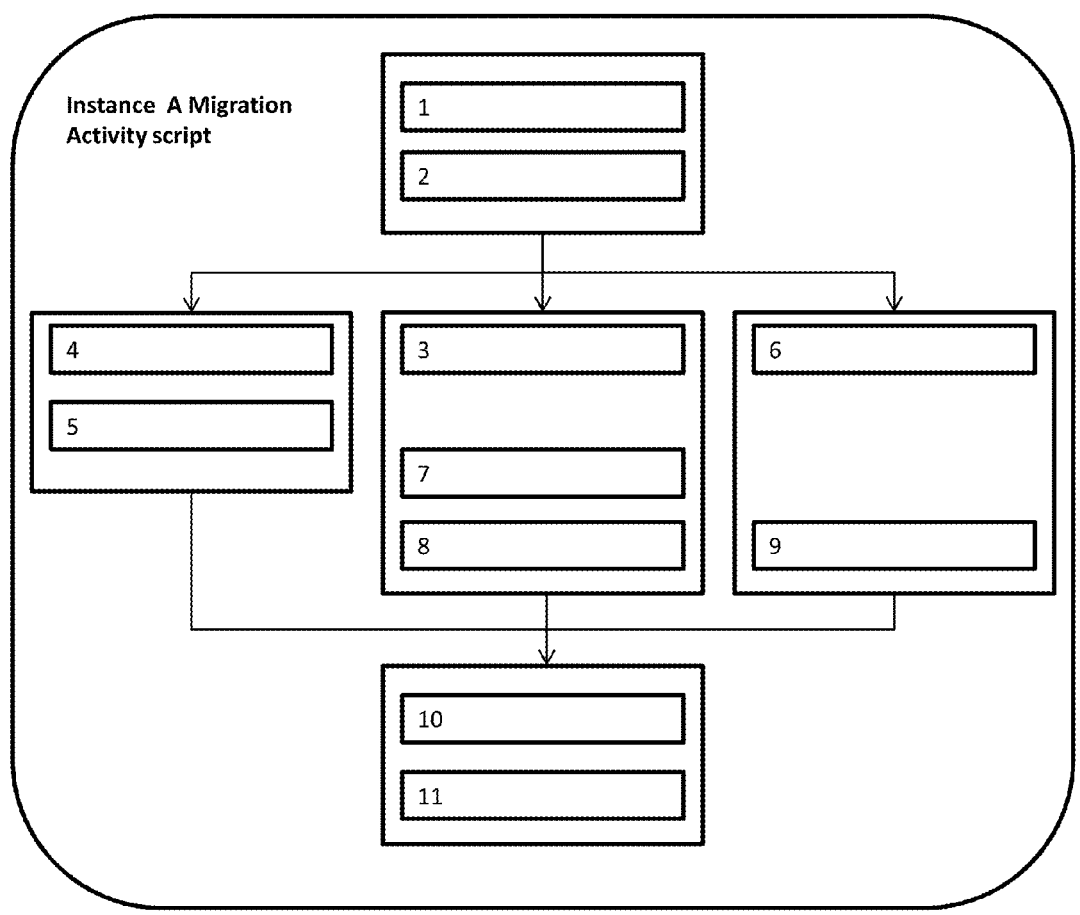
FIG. 6B illustrates exemplary dependency relationships between migration activities of a migration activity script for a common entity, according to the present invention.

For each entity, the migration schedule may further be generated to sequence each migration activity included in the migration activity script for the respective entity. The sequencing of the migration activities within the migration activity script may be determined according to one or more of the sequencing rules described above. For example, one or more migration activities may be grouped together to be accomplished together in parallel, or sequentially according to their numbered order. FIG. 6B illustrates a sequencing of the migration activities that comprise the migration activity script for Instance A. Specifically, FIG. 6B illustrates that migration activities 1-2 are grouped together, migration activities 4-5 are grouped together, migration activities 3, 7, 8 are grouped together, migration activities 6, 9 are grouped together, and migration activities 10-11 are grouped together. Within a specific group, the migration activities may be considered to be dependent on each other as each migration activity within the group must be accomplished before the migration schedule moves on to a next group, or migration activity. Further, FIG. 6 illustrates the sequential dependency amongst the groups in the following way: the group including migration activities 1-2 will be accomplished first, then the group including migration activities 4-5, the group including migration activities 3, 7, 8 and the group including migration activities 6, 9 will be accomplished in parallel, and finally the group including migration activities 10-11 will be accomplished last in the exemplary Instance A migration activity script. Within each group, the migration activities may be accomplished according to their numbered order.

Figure 6C:
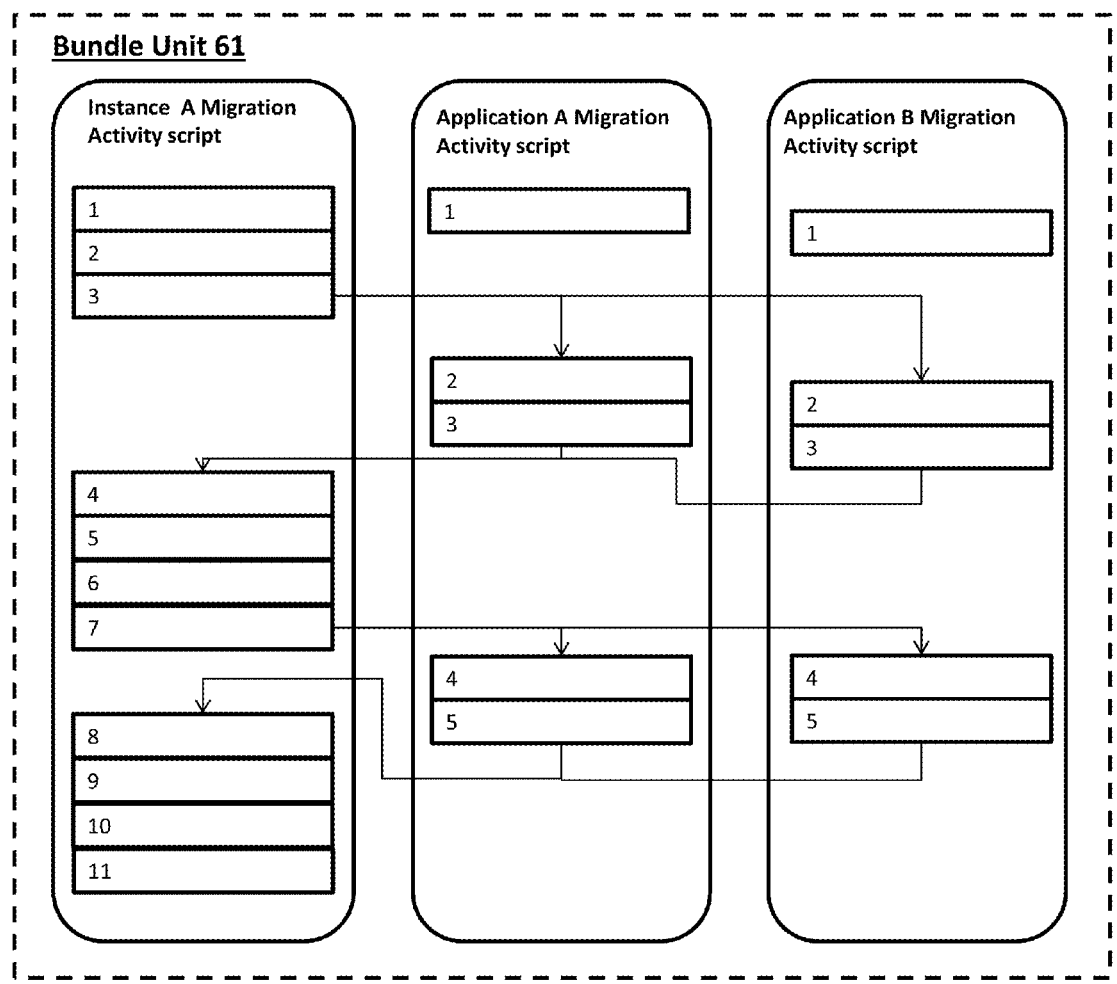
FIG. 6C illustrates exemplary dependency relationships between migration activities across a plurality of migration activity scripts for entities within a common bundle unit, according to the present invention.

On a higher level, the migration schedule may implement sequencing dependencies (i.e., predecessor and successor sequencing rules) across the various migration activities of the different entities within a bundle unit. For example, FIG. 6C illustrates Bundle Unit 61 including the following entities: Instance A, Application A, and Application B. Each entity is shown to have its own set of migration activities for migrating the entity, provided in their respective migration activity scripts. Further, the migration activities across the plurality of entity migration activities scripts are shown to be sequentially dependent. For instance, after migration activity 3 is accomplished in the Instance A migration activity script, migration activity 2 in the Application A migration activity script and migration activity 2 in the Application B migration activity script may be accomplished next. In this case, migration activity 3 in the Instance A migration activity script is the predecessor to migration activity 2 in the Application A migration activity script and migration activity 2 in the Application B migration activity script. FIG. 6C illustrates additional exemplary predecessor and successor sequential relationships amongst the migration activities across the different entity migration activity scripts (i.e., across the different entities) within common bundle unit 61.

In addition or alternatively, one or more of the migration scripts providing instruction sets for managing one or more of the migration activities may be pre-stored in a database. In such cases, the data migration tool may access the database in order to retrieve the pre-stored migration scripts. In any case, the data migration tool may later retrieve the appropriate migration script and present the retrieved migration scripts to the appropriate migration coordinator during the appropriate time. In the case where the migration coordinator is an employee of the client, a migration template may be displayed to the migration coordinator on the display screen of the workstation 100.

Figure 7:
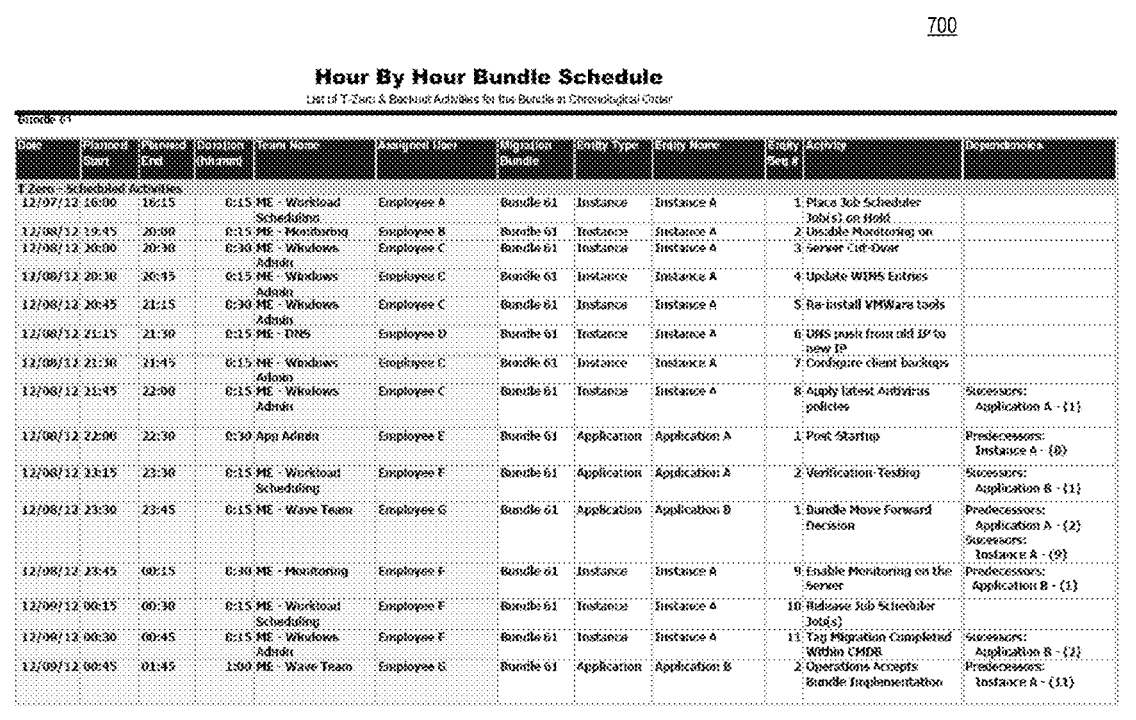

The migration schedule generated by the data migration tool and the data migration activity scripts that are generated as part of the migration schedule may be presented to the client in the form of an hour-by-hour migration schedule that is generated by the data migration tool for each bundle unit. The hour-by-hour migration schedule provides a sequence of migration activities that will need to be accomplished in order to migrate the entities within a particular bundle unit in the sequence determined during the generation of the migration schedule. For example, the hour-by-hour migration schedule may be presented to the client via a graphical interface as illustrated in FIG. 7. The hour-by-hour migration schedule 700 illustrated in FIG. 7 may include a starting date and time for one or more migration activities. The hour-by-hour migration schedule 700 may also include an end time for the one or more migration activities, as well as an estimated duration time for the one or more migration activities.

The hour-by-hour migration schedule 700 may also identify a client side coordinator (e.g., team name, and more specifically the assigned user) that is responsible for completing specific tasks in the data migration project. The hour-by-hour migration schedule 700 may also identify the specific bundle unit (e.g., bundle unit 61) that corresponds to the migration activities. The hour-by-hour migration schedule 700 may also identify an entity type (e.g., Instance or Application) and entity name (e.g., Instance A, Application A, Application B) corresponding to each migration activity. The hour-by-hour migration schedule 700 may also include the sequence number for a corresponding migration activity, where the sequence number identifies an order number of the migration activity amongst a number of migration activities within a respective entity migration activity script.

The hour-by-hour migration schedule 700 may also include information identifying a data migration activity and instructions for detailing how the data migration activity is to be accomplished. The hour-by-hour migration schedule 700 may also include the sequencing rules (e.g., Dependencies) identifying surrounding migration activities that precede and follow the current migration activity, as described above. Although the hour-by-hour migration schedule 700 is described in the form of an hour-by-hour graphical interface illustrated in FIG. 7, it is contemplated that the migration schedule 700 may be generated on any other unit of time basis (e.g., minute-by-minute basis, day-by-day basis, etc.). Also, the information described in the hour-by-hour migration schedule 700 is provided for illustrative purposes only, as the migration schedule may include more, or less, information as illustrated in FIG. 7.

Figure 8:
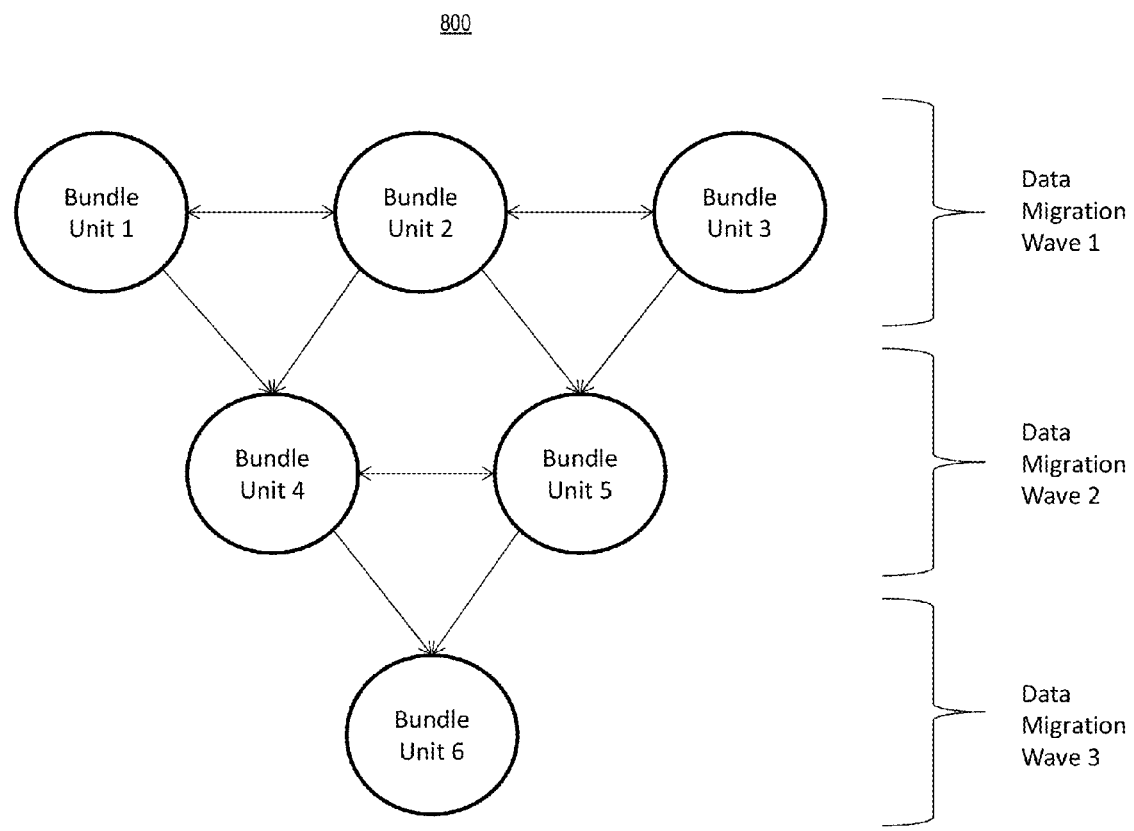
FIG. 8 illustrates an exemplary entity graph describing a relationship between bundle units being migrated in a data migration project, according to the present invention

Based on at least the information gathered from the migration questionnaire and the migration schedule, an entity graph may be generated for sequencing a migration of entities within a bundle unit. The entity graph may further be generated to describe a sequencing of bundle units that will be migrated throughout the data migration project. An exemplary graphical representation of an entity graph 800 is illustrated in FIG. 8. The entity graph 800 provides the relationship of bundle units that will be migrated for the data migration project. Although entity graph 800 is illustrated in terms of bundle units only as nodes, it is contemplated that other types of entities such as applications be placed as nodes within the entity graph 800 (e.g., the entity graph 800 may be generated to map the sequencing of applications within a bundle unit, or to map the sequencing of migration activities across the migration activity scripts for entitles within a bundle unit). The entity graph 800 may be input by the client manually, generated by the data migration tool based on data received from the migration questionnaire and/or migration schedule, or the entity graph 800 may be generated based on a combination of the two. The entity graph 800 is illustrated to have implemented move together rules such that Bundle Units 1-3 are moved together within the common data migration wave 1, Bundle Units 4-5 are moved together within the common data migration wave 2, and Bundle Unit 6 is moved alone in data migration wave 3. The entity graph 800 is also illustrated to have implemented sequencing rules such that data migration wave 1 is migrated before data migration waves 2 and 3, and data migration wave 2 is migrated before data migration wave 3. Data migration wave 3 may be seen to be the implementation of a sequencing rule for migrating data migration wave 3 after data migration waves 1 and 2.

Further description for entity graph 800 is provided with reference to the flowcharts illustrated in FIGS. 9A-9D.

Following the time period $T_{-2}$, the data migration project enters the validation period $T_{-1}$. During the validation period $T_{-1}$, the data migration tool will parse through the entity graph in order to ensure that the entities and data migration waves are structured in accordance to the implemented relationships and various rules described above with regards to the generated migration scheduled and migration schedule. For instance, if at any point the client had manually input the information for generating the entity graph, there is the likelihood that human error may have caused the entity graph to be generated with relationships that are not in accordance to the migration questionnaire and/or migration schedule. In addition or alternatively, additional entities may have been added to the client's data migration project subsequent to the generation of the migration schedule. In such cases, the new entities may need to be incorporated into one or more bundle units in the migration schedule, and subsequently the entity graph, for the data migration.

During the validation period $T_{-1}$, the data migration tool may also parse through each bundle unit as outlined in the entity graph to validate that each bundle unit includes the requisite data in accordance to the rules and relationships implemented by the generated migration schedule and/or migration schedule. For instance, the implemented bundling rules in the generated migration schedule may define bundle unit BU1 as including all application data from a first data server belonging to the client. In this case, the data migration tool may identify this bundling rule indicating that bundle BU1 should include all application data from the first data server and parse bundle unit BU1 to ensure that all of the application data from the first data server is indeed included in bundle unit BU1. If the data migration tool determines that not all of the application data from the first data server is included in the bundle unit BU1, the data migration tool may parse the other bundle units in search of the missing application data. Upon locating application data from the first data server located in another bundle unit, the data migration tool may transfer such application data to the correct bundle unit BU1. In some instances the missing application data may not be found in another bundle unit, but rather may have been simply unaccounted for (e.g., failed to be included in any bundle unit, or newly introduced into the data server). Therefore, the data migration tool may also parse stray application data in a search for the application data from the first data server that should be included as part of bundle unit BU1 as implemented in the generated migration schedule. In some embodiments, the data migration tool may automatically revise the entity graph by updating the bundle units to include their proper applications and/or application data according to bundling rules, move together rules or other relationships between applications implemented by the generated migration schedule.

Alternatively, if the data migration tool identifies a bundling rule, move together rule or other relationship between entities that are not being correctly implemented in the entity graph, the data migration tool may present a flag for the client to recognize. For example, the flag may be a visual indication displayed on a display unit of the workstation 100 that identifies to the client bundle units that are found to violate one or more a rules and/or relationships implemented by the generated migration schedule. In this way, the client may remedy these issues.

During the validation period $T_{-1}$, the data migration tool may also parse through each of the data migration waves outlined in the entity graph in order to validate one or more sequencing rules that have been implemented in the migration schedule. For instance, the entity graph may be parsed in order to validate that data migration waves are scheduled to be migrated in a sequence that abides by wave-based sequencing rules implemented in the migration schedule as described above. Similarly, the data migration tool may parse the entity graph in order to validate that bundle units are scheduled to be migrated in a sequence that abides by bundle unit-based sequencing rules that have been implemented in the migration schedule as described above. In addition, the data migration tool may also parse through the entity graph to validate that bundle units that are scheduled to be migrated together (e.g., move together rules) are included into a common data migration wave, or at least included in data migration waves that are scheduled to be migrated at a same time as required under the implemented sequencing rules of the generated migration schedule.

If the data migration tool identifies bundle units and/or data migration waves that violate any one or more of the sequencing rules implemented in the generated migration schedule, the data migration tool may automatically revise the entity graph by rearranging the bundle units or migration waves to abide by the implemented sequencing rules of the generated migration schedule.

Alternatively, if the data migration tool identifies a sequencing rule that is not being correctly implemented in the entity graph, the data migration tool may present a flag for the client to recognize. For example, the flag may be a visual indication displayed on a display unit of the workstation 100 that identifies to the client that one or more bundle units and/or data migration waves are found to violate one or more sequencing rules implemented by the generated migration schedule. In this way, the client may remedy these issues.

During the validation period $T_{-1}$, the data migration tool may also uncover loops in the entity graph that may result in the disruptive situation where the data migration becomes stuck in an infinite loop that will not allow the data migration to proceed to a next entity or data migration wave from being migrated. An unwanted loop may occur in the entity graph due to improper sequencing rules that force the data migration to abide by the sequencing rules during the data migration process. For example, the sequencing rules may be generated such that the sequence of bundle units to be migrated gets stuck in a loop that cannot progress to a next bundle unit. Therefore, the data migration tool may parse the entity graph during the validation period $T_{-1}$, in order to uncover these unwanted loops and fix them to allow the migration process to progress through all of the entities of the data migration project.

Alternatively, the data migration tool may identify any discovered loops and present a flag for the client to recognize. For example, the data migration tool may display a visual flag on a display unit of the workstation 100 in order for the client to recognize the loop and take measures to fix the loop before commencing the data migration. In this way, the client may remedy these issues.

Following the planning and bundling period $T_{-2}$ and validation period $T_{-1}$, the data migration project will be ready to start the data migration portion at the data migration period $T_0$. The data migration portion of the data migration project will be implemented by migrating the entities in their corresponding data migration waves according to the migration schedule that is generated earlier. For example, the data migration may be implemented by following the migration activities as described, and in the order, provided in the migration schedule (e.g., as illustrated by the hour-by-hour schedule in FIG. 7).

During the data migration period $T_0$, the data migration tool may monitor the data migration to ensure that the data migration is proceeding according to the migration schedule.

For instance, the data migration tool may be monitoring the data migration to ensure that predecessor-successor relationships (e.g., sequencing rules) between data migration waves, bundle units and/or entities within a bundle unit are being maintained as implemented in the generated migration schedule. If during the data migration period $T_0$ the data migration tool detects that data migration waves, bundle units and/or entities within a bundle unit are being migrated in a sequence that violates any one or more of the predecessor-successor relationships, the data migration tool may provide a flag for the client that identifies the one or more sequencing rules being violated. For example, the data migration tool may provide a visual flag displayed on a display unit of the workstation 100 that identifies the specific sequencing rule being violated, as well as the data migration wave and/or bundle units that are violating the sequencing rule.

Alternatively, the data migration tool may halt the data migration. During the time that the data migration is halted, the data migration tool may reorganize the sequence of data migration waves, bundle units and/or entities within a bundle unit in accordance to the entity graph, and then resume the data migration process.

The data migration tool may also be monitoring the data migration in order to ensure that bundling rules and/or move together rules implemented in the migration schedule are being followed. If during the data migration period $T_0$ the data migration tool detects that one or more bundling rules and/or move together rules are not being followed, the data migration tool may provide a flag for the client that identifies the one or more bundling rules and/or move together rules not being followed. For example, the data migration tool may provide a visual flag displayed on a display unit of the workstation 100 that identifies the specific bundling rules and/or move together rules not being followed, as well as the specific data migration waves, bundle units and/or entities within a bundle unit that are violating the specific bundling rules and/or move together rules.

Alternatively, if during the data migration period $T_0$ the data migration tool detects that one or more bundling rules, and/or move together rules are not being followed, the data migration tool may halt the data migration. During the time that the data migration is halted, the data migration tool may reorganize the sequence of data migration waves, bundle units and/or entities within a bundle unit in accordance to the bundling rules and/or move together rules that were implemented in the generated migration schedule, and then resume the data migration process.

The data migration tool may also be monitoring the data migration in order to ensure that each bundle unit contains the correct entities as identified in the relationships between entities implemented in the migration schedule. If during the data migration period $T_0$ the data migration tool detects that a bundle unit does not include all of the entities it should include according to the migration schedule, the data migration tool may provide a flag for the client that identifies the one or more entities that are not following the relationship rules implemented in the migration schedule. For example, the data migration tool may provide a visual flag displayed on a display unit of the workstation 100 that identifies the specific entities that are not following the relationship rules implemented in the migration schedule.

Alternatively, if during the data migration period $T_0$ the data migration tool detects that a bundle unit does not include all of the entities it should include according to the migration schedule, the data migration tool may halt the data migration. During the time that the data migration is halted, the data migration tool may parse through other bundle units in search of the entities that should have been included in the bundle unit. Upon locating such entities, the data migration tool may reorganize the bundle units by including the entities into its appropriate bundle unit as outlined in the migration schedule. After reorganizing the entities, the data migration tool may then resume the data migration process.

Similarly, in the case where the data migration tool detects that a bundle unit includes entities that does not belong within the bundle unit according to the migration schedule, the data migration tool may provide a flag for the client that identifies the one or more entities that are incorrectly included in a bundle unit in view of the relationship rules implemented in the migration schedule. For example, the data migration tool may provide a visual flag displayed on a display unit of the workstation 100 that identifies the specific entities that are incorrectly included in a bundle unit in view of the relationship rules implemented in the migration schedule.

Alternatively, if during the data migration period $T_0$ the data migration tool detects that a bundle unit includes one or more entities it should not include according to the migration schedule, the data migration tool may halt the data migration. During the time that the data migration is halted, the data migration tool may reference the migration schedule in order to obtain information on which bundle unit the mistaken entities belongs to, and then locate the appropriate bundle unit within the data migration project. The data migration tool may then reorganize the entities such that the mistaken entities is included as part of the appropriate bundle data. After reorganizing the entities, the data migration tool may then resume the data migration process. In case the appropriate bundle unit has already been migrated, the data migration tool may determine the destination location of the appropriate bundle unit, and migrate (e.g., transmit) the mistaken entities to the destination location of the appropriate bundle unit. The destination location may generally be a destination data storage system, or more specifically the destination data server within the destination data storage system.

In addition to the features of the data migration tool that are available during the data migration period $T_0$ as described above, the data migration tool may also provide the client with estimates for when each migration activity during the data migration portion will be finished. The data migration tool may also provide the client with a time at which future data migration activities will commence. The timing information may be presented to the client via a message that is displayed on a display unit of the workstation 100.

If any issues occur during the data migration period $T_0$, the data migration tool may detect such issues occurring, or at least be notified of such issues occurring, and recalculate anticipated migration activity start and finish times accordingly. The recalculated migration activity start and finish times may then be presented to the client (e.g., displayed on the workstation 100). For example, if migration activity 1 is originally scheduled to start at 10:00 a.m. and an unexpected issue occurs prior to migration activity 1 that lasts for one (1) hour, the data migration tool may detect such issue occurring, and/or the data migration tool may be notified of such issue, and the data migration tool may recalculate the anticipated start time for migration activity 1 to be 11:00 a.m. The data migration tool may further provide a message to the client via the workstation 100 of this new start time for migration activity 1 to indicate it has been pushed back one (1) hour due to the unexpected issue. It follows that the data migration tool may also provide a similar message to the client informing the client that the anticipated end time for migration activity 1 is pushed back one (1) hour due to the same issue.

Figure 9A:
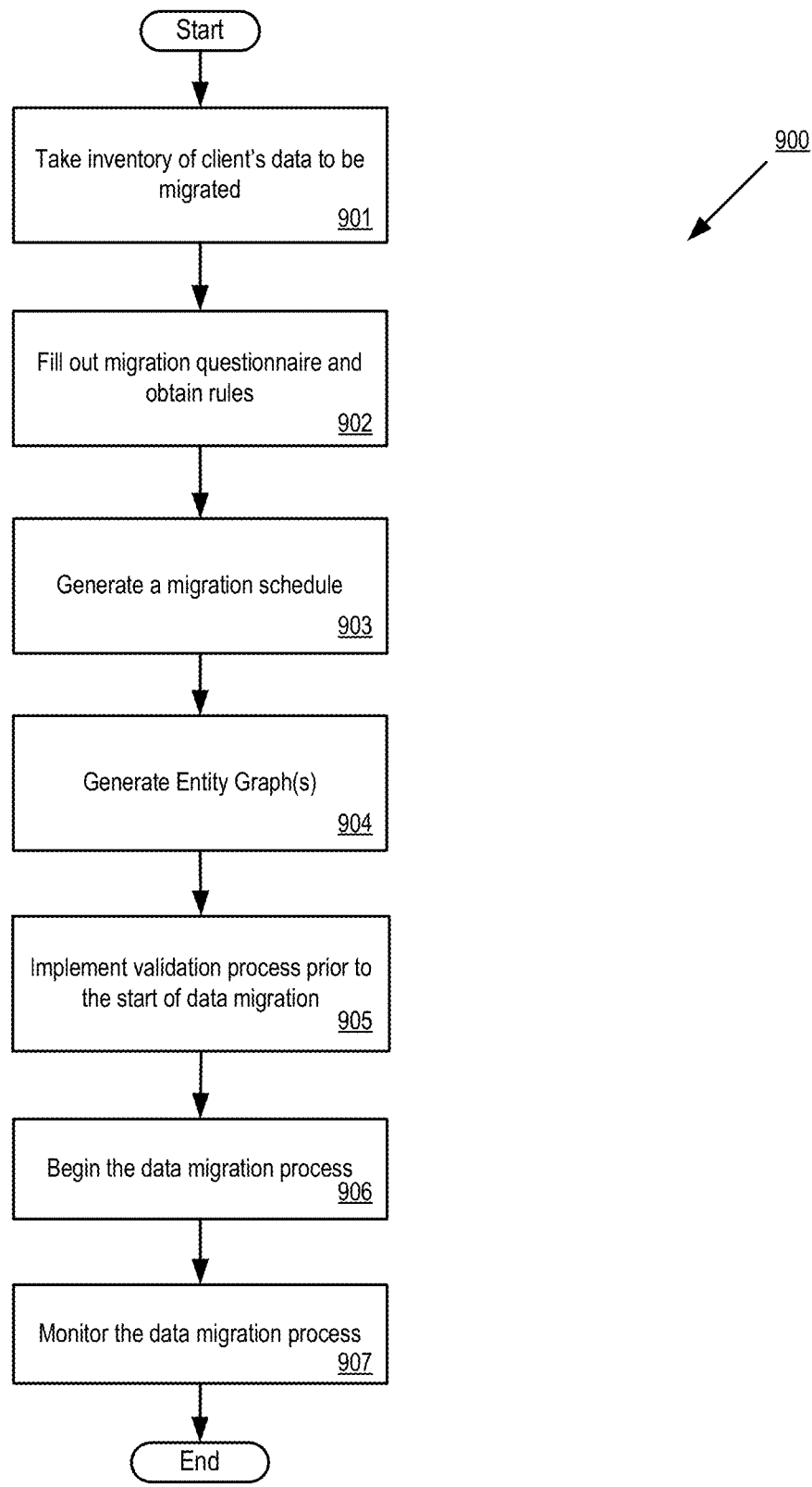
FIG. 9A illustrates a flow chart describing a process for executing a data migration project according to the present invention.

FIG. 9A illustrates an exemplary flow chart 900 describing a process for implementing a data migration project according to the features described above.

At 901, inventory of a client's data to be migrated according to the data migration project may be taken. The inventory will take into account the client's applications and other data to be migrated, the client's servers that currently store the applications and other data to be migrated. The inventory may also identify certain relationships shared between applications that will be migrated, as well as provided initial classifications for applications that will be migrated. The inventory may also identify a number of client servers storing applications to be migrated that will need to be considered for the data migration project. The description of the inventory process may be further supplemented by the description provided above.

At 902, a migration questionnaire is presented to the client for the client to fill out. The migration questionnaire may ask the client to provide any of the information as described above with reference to the processes implemented during the planning and bundling period $T_{-2}$ illustrated in FIG. 3. From the information provided by the client into the migration questionnaire, a set of one or more bundling, move together, and sequencing rules may be obtained at 902.

At 903, a migration schedule may be generated by the data migration tool being executed on, for example, the workstation 100 described above. The migration schedule may be generated according to any one or more of the features and rules described above with reference to the processes implemented during the planning and bundling period $T_{-2}$ illustrated in FIG. 3. The data migration tool may additionally take into consideration the client's scheduling information when generating the migration schedule. The client's scheduling information may identify the client's preferred start and/or end times for one or more specific migration tasks, as well as identify times when the client will be available to monitor specific migration tasks. So the migration schedule that is generated by the data migration tool may satisfy one or more, and up to all, of the rules and relationships input by the client during the inventory and migration questionnaire processes at 901 and 902, respectively. In addition to the rules and relationships identified in

901 and 902, the data migration tool may additionally take into consideration the client's scheduling information against the identified rules and relationships.

In this way, the migration schedule may be generated to include a start and end time for one or more data migration waves of data that will comprise the data migration portion of the data migration project. The migration schedule may also be generated to identify a destination data storage system for migrating one or more of the bundle units of application data in the data migration project. The migration schedule may also be generated to include a list of migration activities that comprises the data migration project, as well as providing a sequencing of the migration activities. The migration schedule may also include one or more migration activity scripts for providing instructions describing how each migration activity is to be managed and completed. The description of the generated migration schedule may be further supplemented by the description provided above.

Figure 9B:
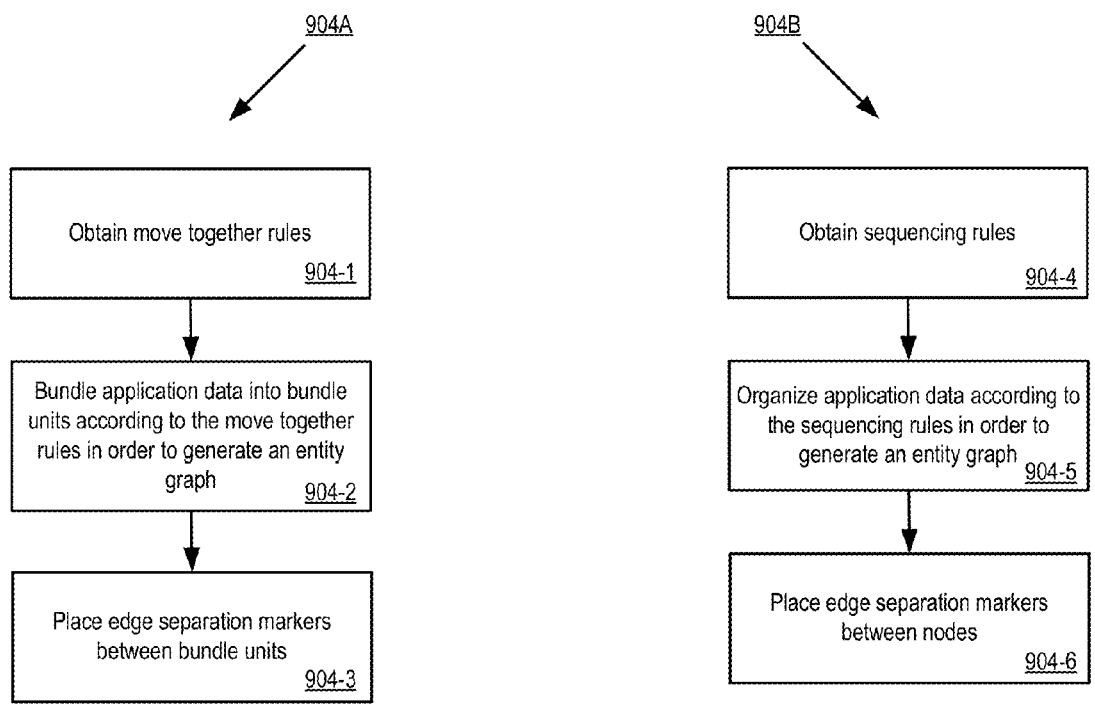
FIG. 9B illustrates a more detailed view of a process included in the flow chart illustrated in FIG. 9A.

At 904, one or more entity graphs may be generated according to any one or more of the features described above with reference to the processes implemented during the planning and bundling period $T_{-2}$ illustrated in FIG. 3. FIG. 9B provides a more detailed view of the processes involved for generating one or more entity graphs at 904. FIG. 9B will be described in more detail later in this disclosure.

Figure 9C:
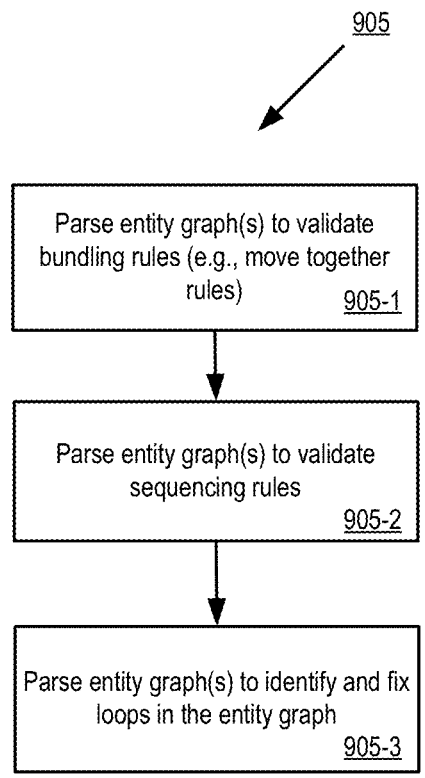
FIG. 9C illustrates a more detailed view of a process included in the flow chart illustrated in FIG. 9A.

At 905, a validation process may be implemented according to any one or more of the features described above with reference to the processes implemented during the validation period $T_{-1}$ described above. FIG. 9C provides a more detailed view of the processes involved during the validation period at 905 that are implemented prior to the start of the data migration. FIG. 9C will be described in more detail later in this disclosure.

At 906, the data migration process begins. The data migration may be implemented according to the migration schedule generated at 903.

Figure 9D:
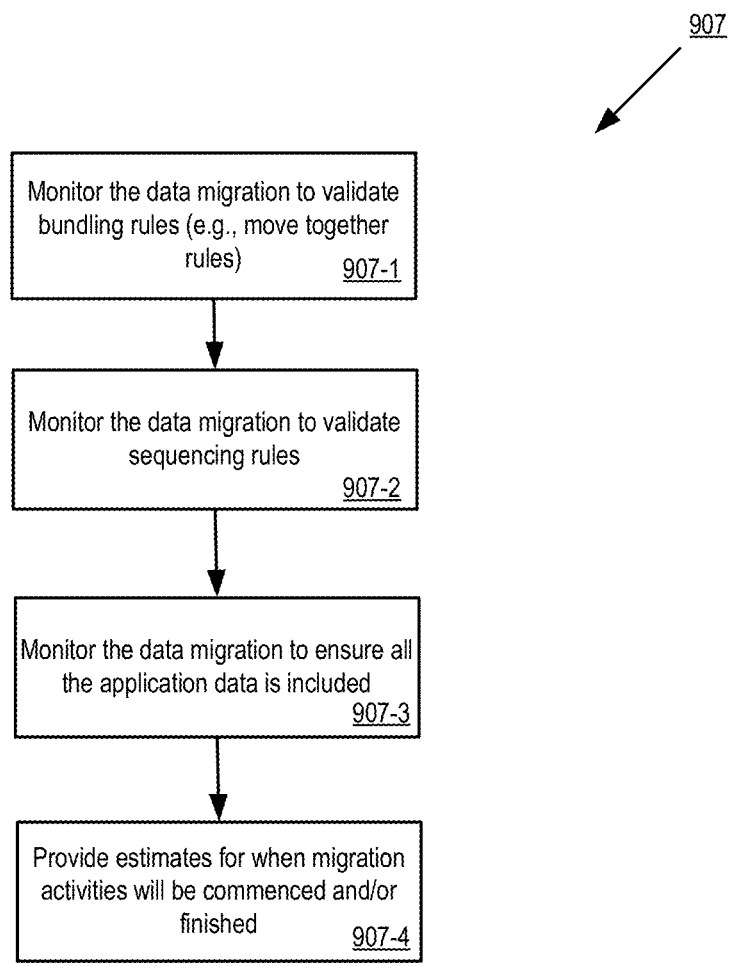
FIG. 9D illustrates a more detailed view of a process included in the flow chart illustrated in FIG. 9A.

At 907, concurrent with the start of the data migration process, or shortly thereafter, the data migration tool will begin to monitor the data migration process. The monitoring processes at 907 may be implemented according to any one or more of the features described above with reference to the processes implemented during the data migration period $T_0$ described above. FIG. 9D provides a more detailed view of the processes involved during the data migration period at 907. FIG. 9D will be described in more detail later in this disclosure.

FIG. 9B illustrates a flow chart 904A that describes a process for generating an entity graph based on move together rules implemented in the generated migration schedule. The move together rules are described in detail above. Although flow chart 904A is described in terms of organizing bundle units into the entity graph, the nodes of the entity graph may be applications, or other entities, within a common bundle unit. The nodes may also be individual migration activities that comprise the migration activity scripts for the entities within a common bundle unit.

At 904-1, the move together rules that are implemented in the generated migration schedule may be obtained. At 904-2, the move together rules may be referenced by the data migration tool in order to bundle the application data into bundle units according to the move together rules. Each bundle unit will be comprised of application data that are identified as being migrated together in the migration schedule. For example, a move together rule may identify application data stored on a common source data server as being organized into a common bundle unit to be migrated together. A move together rule may also identify that application data related to a common shared service will be organized into a common bundle unit to be migrated together. The application data related to the common shared service may be store on one source data server, or across more than one source data server. A move together rule may also identify that application data stored on one or more specified source data server will be organized into a common bundle unit to be migrated together. Application data and/or source data servers that are identified by move together rules as migrating within a common bundle unit may be identified with a move together flag.

By bundling the application data into bundle units according to the move together rules, a move together rules (MTR) based entity graph may also be generated at 904-2. Each bundle unit that is mapped into the MTR based entity graph will identify the application data and/or source data server that comprise it. Each bundle unit that is mapped into the MTR based entity graph may also identify a corresponding move together flag.

At 904-3, edge separation markers may be placed in between bundle units to further distinguish each bundle unit. This feature may be optionally applied.

FIG. 9B illustrates a flow chart 704B that describes a process for generating an entity graph based on sequencing rules implemented in the generated migration schedule. The sequencing rules are described in detail above. Although flow chart 904A is described in terms of organizing bundle units into the entity graph, the nodes of the entity graph may be applications, or other entities, within a common bundle unit. The nodes may also be individual migration activities that comprise the migration activity scripts for the entities within a common bundle unit.

At 904-4, the sequencing rules that are implemented in the generated migration schedule may be obtained. At 904-5, the sequencing rules may be referenced by the data migration tool in order to bundle the application data into bundle units according to the sequencing rules. The sequencing rules may identify one or more specific predecessor and successor relationships between application data, bundle units, and/or data migration waves. For example, a sequencing rule may identify a sequence in which specified application data is to be migrated with relation to other specified application data. A sequencing rule may also identify a sequence in which specified bundle units are to be migration with relation to other specified bundle units. A sequencing rule may also identify a sequence in which specified data migration waves may be migrated with relation to other specified data migration waves.

By organizing the application data according to the sequencing rules, a sequencing rules based entity graph may also be generated at 904-5. The sequencing rules based entity graph may be organized into a data tree structure where each application data, bundle unit, source data server and/or data migration wave that is identified by a sequencing rule is a node in the data tree. For example, FIG. 8 illustrates a data tree 800 that describes exemplary sequential relationships that may be identified by sequencing rules. Each bundle unit illustrated in the data tree 800 may be considered a node in the data tree 800.

Bundle units 1, 2 and 3 are described as being migrated at a same time, in parallel. These sequencing rules are illustrated by the arrows between bundle units 1, 2, and 3. Further, bundle units 1, 2 and 3 are illustrated in the data tree 800 as being part of the same data migration wave 1.

The sequencing rules may also identify that bundle units 1, 2 and 3 are to be migrated before bundle units 4 and 5. The sequencing rules may even identify that bundle units 1, 2 and 3 are to be migrated before bundle unit 6 (although this is not specifically illustrated in the data tree 800). Conversely, the sequencing rules may identify that bundle units 4 and 5 are to be migrated after bundle units 1, 2 and 3. In either case, these sequencing rules are illustrated by the arrows extending from bundle units 1, 2 and 3 to bundle units 4 and 5.

The sequencing rules may also identify that bundle units 4 and 5 are to be migrated at a same time, in parallel. These sequencing rules are illustrated by the arrows between bundle units 4 and 5. Further, bundle units 4 and 5 are illustrated in the data tree 800 as being part of the same data migration wave 2.

The sequencing rules may also identify that bundle units 4 and 5 are to be migrated before bundle unit 6. Conversely, the sequencing rules may identify that bundle unit 6 is to be migrated after bundle units 4 and 5. In either case, these sequencing rules are illustrated by the arrows extending from bundle units 4 and 5 to bundle unit 6.

Bundle unit 6 may be identified in the sequencing rules as migrating alone as part of data migration wave 3.

Although the data tree 800 is illustrated as having each node represented by a bundle unit, this representation is provided for illustrative purposes only. It is contemplated that the nodes of a data tree be comprised of any combination of application data, bundle units, data servers, data migration waves and/or other type of entity contemplated throughout this disclosure.

At 904-6, edge separation markers may be placed in between nodes in the data tree to further distinguish each node from another node. This feature may be optionally applied.

In some embodiments, the move together rules based entity graph may be generated before the sequencing rules based entity graph. In some embodiments, the move together rules based entity graph and the sequencing rules based entity graph may be combined. For example, the bundle units that may comprise a node in the sequencing rules based entity graph may be obtained from a bundle unit generated as part of a move together rules entity graph.

Alternatively, the move together rules based entity graph may be generated in parallel to the sequencing rules based entity graph.

FIG. 9C illustrates a more detailed view for the processes that may be implemented during the validation process at 905 in flow chart 900. During the validation process at 905, the data migration tool may implement one or more of the features described above with reference to the validation period $T_{-1}$ described above.

For example, at 905-1 the data migration tool may parse the previously generated entity graphs(s) in order to validate that the bundling rules are being properly applied. So if the bundling rules included a move together rule, the data migration tool may parse the entity graph(s) to ensure that the application data, bundle units, and/or data migration waves that comprise the entity graph(s) are organized according to the move together rule. This validation may be needed to check for new or unaccounted for application data that may have entered the data migration project since the generation of the entity graph(s), or to account for human errors that may have occurred during the generation of the entity graph(s).

At 905-2, the data migration tool may parse the entity graph(s) in order to validate that the sequencing rules are being properly applied. For example, if the sequencing rules called for the application data, bundle units and/or data migration waves to have predecessor and successor relationships as illustrated in the data tree 800 of FIG. 8, the data migration tool may parse through the entity graph(s) to ensure the entity graph(s) do indeed abide by the sequencing rules. This validation may be needed to check for new or unaccounted for application data that may have entered the data migration project since the generation of the entity graph(s), or to account for human errors that may have occurred during the generation of the entity graph(s).

Figure 10:
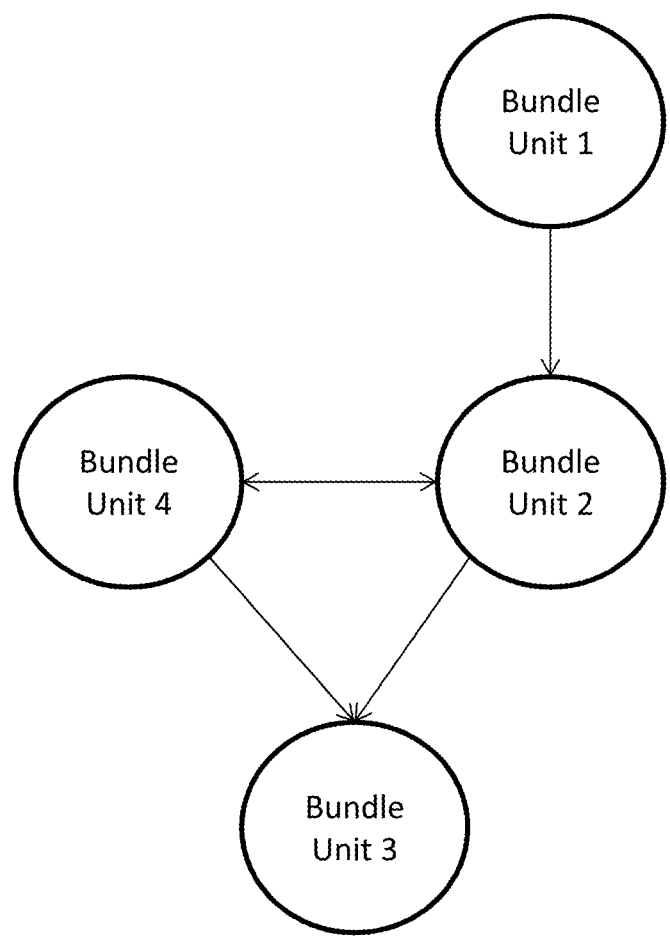
FIG. 10 illustrates an exemplary data tree loop portion according to the present invention.

At 905-3, the data migration tool may parse the entity graph(s) in order to identify and fix any loops that may exist in the entity graph(s). For example, FIG. 10 illustrates at least a portion of a data tree 1000 that includes an unwanted loop. The loop may be the result of sequencing rules being applied to new or unaccounted for application data. Or the loop may be the result of faulty sequencing rules being input by the client. In either case, the loop is undesirable because the data migration will be halted at this loop portion as the data migration will not be able to exit the loop and proceed to a next application data, bundle unit and/or data migration wave to migrate. The data tree 1000 is organized such that a bundle unit 1 is migrated, and then a sequencing rule calls for bundle unit 2 to be migrated after bundle unit 1. Then a sequencing rule calls for bundle unit 3 to be migrated after bundle unit 2. Then a sequencing rule calls for bundle unit 4 to be migrated after bundle unit 3. And then a sequencing rule calls for bundle unit 2 to be migrated after bundle unit 4 (e.g., this sequencing rule is the cause of the undesirable loop). In this case, the data migration tool may identify the undesirable loop that involves bundle units 2-4 and fix it. The data migration tool may be able to fix the loop by amending the sequencing rule that states bundle unit 2 is to be migrated after bundle unit 4, to now state that bundle unit 5 (not illustrated) is to be migrated after bundle unit 4. By amending this sequencing rule responsible for the undesirable loop, the data migration tool is able to re-start the data migration to get out from the loop.

Alternatively, the data migration tool may identify any discovered loops and present a flag for the client to recognize. As an option, the data migration tool may also concurrently halt the data migration project until the client addresses this issue. For example, the data migration tool may display a visual flag on a display unit of the workstation 100 in order for the client to recognize the loop and take measures to fix the loop before commencing the data migration. In this way, the client may remedy these issues. Although each node in the data tree 1000 was described as being a bundle unit, it is contemplated that the nodes may be comprised of any one or more of the entities described throughout this disclosure.

Although not specifically illustrated, following 905-3, the data migration tool may parse the entity graph(s) to ensure that all of the application data, bundle units and/or data migration waves that are intended to be part of the data migration project are included in the entity graph(s). If the data migration tool detects a discrepancy between the application data, bundle units and/or data migration waves that are intended to be part of the data migration project and what is included in the entity graph(s), the data migration tool may modify the entity graph to fix the discrepancies. The data migration tool may modify the entity graph by modifying the application data included in the bundle units and/or data migration waves to follow the various rules as described above. The data migration tool may also modify the entity graph by modifying the bundle units included in the data migration waves to follow the various rules as described above. This process may be optionally included to provide an added level of security.

Although not specifically illustrated, following 905-3, the data migration tool may parse the entity graph(s) in order to monitor the destinations that are set for each application data, bundle unit and/or data migration wave in the entity graph(s). If the data migration tool detects any of the application data, bundle units and/or data migration waves are identified in the entity graph(s) as being migrated to a destination location that does not correlate to a proper destination location identified from the migration questionnaire and/or migration schedule, the data migration schedule may revise the entity graph(s) to identify the proper destination locations. This process may be optionally included to provide an added level of security.

In some embodiments, the destination location for the application data, bundle unit and/or data migration wave may not be included in the entity graph(s), but rather may remain as part of the migration schedule. In such embodiments, the data migration tool may parse the migration schedule to detect any application data, bundle units and/or data migration waves that are destined to be migrated to a wrong destination location. The data migration tool may then revise the migration schedule to identify the proper destination location.

FIG. 9D illustrates a more detailed view for the processes that may be implemented during the monitoring process at 907 in flow chart 900. During the monitoring process at 907, one or more of the features described above with reference to the monitoring executed by the data migration tool during the data migration period $T_{-0}$ described above may be implemented.

At 907-1, the data migration tool may monitor the data migration in order to validate that the bundling rules are being properly applied. So if the bundling rules included a move together rule, the data migration tool may monitor the data migration to ensure that the application data, bundle units, and/or data migration waves that comprise the entity graph(s) are being migrated according to the move together rule. This monitoring may be needed to check for new or unaccounted for application data that may have entered the data migration project since the generation of the entity graph(s), or to account for human errors that may have occurred during the generation of the entity graph(s). If a bundling rule is found to be violated, the data migration tool may provide a message to the client that identifies the bundling rule being violated and/or the specific bundle units that are violating the identified bundling rule. For example, the message may be provided to the client by displaying the message on a display unit of the workstation 100.

At 907-2, the data migration tool may monitor the data migration in order to validate that the sequencing rules are being properly applied. For example, if the sequencing rules called for the application data, bundle units and/or data migration waves to have predecessor and successor relationships as illustrated in the data tree 800 of FIG. 8, the data migration tool may monitor the data migration to ensure the entity graph(s) are indeed being migrated according to the sequencing rules. This monitoring may be needed to check for new or unaccounted for application data that may have entered the data migration project since the generation of the entity graph(s), or to account for human errors that may have occurred during the generation of the entity graph(s). If a sequencing rule is found to be violated, the data migration tool may provide a message to the client that identifies the sequencing rule being violated and/or the specific bundle units and/or data migration waves that are violating the identified sequencing rule. For example, the message may be provided to the client by displaying the message on a display unit of the workstation 100.

At 907-3, the data migration tool may monitor the data migration to ensure that all of the application data, bundle units and/or data migration waves that are intended to be part of the data migration project are migrated during the data migration. If the data migration tool detects a discrepancy between the application data, bundle units and/or data migration waves that are intended to be part of the data migration project and what is actually migrated, the data migration tool may provide a message to the client that identifies this issue. For example, the message may be provided to the client by displaying the message on a display unit of the workstation 100.

At 907-4, the data migration tool may provide an anticipated start and finish time for one or more data migration activities, as well as an estimate on an overall time to complete the data migration. The data migration tool is able to provide these estimates based on estimated calculations for the time it will take to accomplish one or more of the data migration activities/tasks that are identified in the migration schedule. In addition, if the client has previously indicated, for example in the migration questionnaire, that the data migration project is needed to be completed by a certain date or within a certain amount of time, the data migration tool may be able to modify the entity graph (e.g., data graph) to better accomplish these time goals input by the client. If the current time estimate for completing the data migration project is calculated to be greater than an amount of time desired by the client, the data migration tool may modify the entity graph by modifying sequencing rules, bundling rules, bundle units and/or migration waves in order to achieve the data migration project within the time constraints identified by the client. For example, the data migration tool may modify the sequencing rules such that additional bundle units are added to a given migration wave. By adding additional bundle units to a given migration wave, the total number of migration waves may be decreased by having more bundle units migrated in parallel as opposed to in series, which in turn may result in the decrease in the overall data migration process.

In addition, the data migration tool may detect issues that may occur during the data migration project and recalculate anticipated start and finish times for specific data migration activities based on the detection of these issues. The data migration tool may then present these recalculated anticipated start and finish times for specific data migration activities to the client (e.g., display the new start and finish times on the workstation 100).

Although the features of 907-4 have been illustrated as taking place during the monitoring of the data migration process, it is contemplated that the features of 907-4 are also made available as part of the processes described as comprising the validation processes at 905 in flowchart 900.

Also, the sequencing order of processes that are illustrated in FIGS. 9B-9D are provided for exemplary purposes only, and other sequence orders are contemplated.

The illustrations described herein are intended to provide a general understanding of the structure of various embodiments. The illustrations are not intended to serve as a complete description of all of the elements and features of apparatus, processors, and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Additionally, the illustrations are merely representational and cannot be drawn to scale. Certain proportions within the illustrations may be exaggerated, while other proportions may be minimized. Accordingly, the disclosure and the figures are to be regarded as illustrative rather than restrictive.

The above disclosed subject matter is to be considered illustrative, and not restrictive, and the appended claims are intended to cover all such modifications, enhancements, and other embodiments, which fall within the true spirit and scope of the description. Thus, to the maximum extent allowed by law, the scope is to be determined by the broadest permissible interpretation of the following claims and their equivalents, and shall not be restricted or limited by the foregoing detailed description.

What is claimed is:

1. A method of implementing a data migration project for migrating a plurality of applications from a source data storage system to a destination data storage system, the method comprising:
   receiving, at a controller, a set of data migration rules, the data migration rules comprising:
      a bundling rule indicating that a first subset of applications of the plurality of applications are to be grouped in a single bundle unit;
      a move together rule indicating that at least two applications are to be migrated in a single migration wave; and
      a sequencing rule indicating that a first application is to be migrated prior to beginning migration of a second application;
   receiving, at the controller, a set of scheduling considerations;
   receiving, at the controller, a precedence flag for at least one individual data migration rule or scheduling consideration, the precedence flag indicating that the at least one individual data migration rule or scheduling consideration must be implemented in a migration schedule over another data migration rule or scheduling consideration;
   comparing, by the controller, the set of data migration rules against the set of scheduling considerations;
   determining, by the controller, that a conflict exists between the data migration rules and the scheduling considerations;
   selecting, by the controller, at least a first data migration rule corresponding to the precedence flag to implement over a scheduling consideration based on the determination that the conflict exists;
   grouping, by the controller, applications on the source data storage system in to a bundle unit according to the bundling rule and at least the first data migration rule while ignoring the scheduling consideration; and
   generating, by the controller, a migration schedule for migrating the bundle unit according to the move together rule, the sequencing rule, and at least the first data migration rule while ignoring the scheduling consideration.

2. The method of claim 1, wherein generating the migration schedule comprises implementing sequential relationships between entities within the set of application data, and the method further comprises:
   determining one or more data migration activities that correspond to an entity such that the entity is migrated according to the one or more data migration activities.

3. The method of claim 2, wherein the one or more data migration activities identify a set of instructions for migrating the corresponding entity.

4. The method of claim 2, wherein generating the migration schedule comprises identifying at least a start time and end time for a corresponding data migration activity.

5. The method of claim 1,
   wherein a migration activity script is generated for one or more of the applications within the bundle unit such that each migration activity script is comprised of one or more migration activities that identify a set of instructions for migrating a corresponding application.

6. The method of claim 5, wherein generating the migration schedule further comprises implementing a sequence in which the migration activities within the migration activity script are to be accomplished.

7. The method of claim 5, wherein generating the migration schedule further comprises implementing a sequence in which the migration activities are to be accomplished for each migration activity script.

8. The method of claim 7, wherein the sequence identifies dependency relationships between migration activity scripts such that a next migration activity in a second migration activity script cannot be commenced until a previous migration activity in a first migration activity script is accomplished.

9. The method of claim 1, further comprising:
   identifying one or more stray application data not associated with any bundle units, and
   associating the one or more stray application data to one or more bundle units according to data migration rules implemented in the migration schedule.

10. The method of claim 1, further comprising:
    migrating the set of application data according to the migration schedule;
    comparing the one or more bundle units against the set of data migration rules implemented in the migration schedule; and
    determining whether any of the one or more bundle units violate data migration rules implemented in the migration schedule based on the comparison.

11. The method of claim 10, further comprising:
    providing an indication that identifies at least one of the one or more bundle units that violate data migration rules implemented in the migration schedule or the violated data migration rules implemented in the migration schedule.

12. The method of claim 1, wherein a data migration rule requires application data stored on a common data storage server to be included in a common bundle unit.

13. The method of claim 1, wherein a data migration rule requires application data related to a common shared service to be included in a common bundle unit.

14. The method of claim 1, wherein the sequencing rule identifies an order in which applications, bundle units or data migration waves are to be migrated from a source data server to a destination data server.

15. A workstation for implementing a data migration project for migrating a plurality of applications from a source data storage system to a destination data storage system, the workstation comprising:
    a memory configured to store:
       a set of data migration rules and a set of scheduling considerations, the set of data migration rules comprising:
          a bundling rule indicating that a first subset of applications of the plurality of applications are to be grouped in a single bundle unit;
          a move together rule indicating that at least two applications are to be migrated in a single migration wave; and a sequencing rule indicating that a first application is to be migrated prior to beginning migration of a second application; and a precedence flag for at least one individual data migration rule or scheduling consideration, the precedence flag indicating that the at least one individual data migration rule or scheduling consideration must be implemented in a migration schedule over another data migration rule or scheduling consideration; and a controller configured to:

compare the set of data migration rules against the set of scheduling considerations;

determine that a conflict exists between the data migration rules and the scheduling considerations;

select at least a first data migration rule corresponding to the precedence flag to implement over a scheduling consideration based on the determination that the conflict exists;

identify applications on a common server and sharing a common service;

group the identified applications and corresponding application data in to a bundle unit according to the bundling rule and at least the first data migration rule while ignoring the scheduling consideration; and generate a migration schedule for migrating the bundle unit according to the move together rule, the sequencing rule, and at least the first data migration rule while ignoring the scheduling consideration.

16. The workstation of claim 15, wherein the migration schedule identifies one or more migration activities and corresponding scheduling information for the one or more migration activities.

17. A non-transitory computer readable memory storing instructions for implementing a data migration project for migrating a plurality of applications from a source data storage system to a destination data storage system, the computer readable memory comprising a set of instructions executable by a processor the set of instructions comprising:

instructions to store a set of data migration rules, a set of scheduling considerations, and a precedence flag for at least one individual data migration rule or scheduling consideration, wherein the data migration rules comprise:

a bundling rule indicating that a first subset of applications of the plurality of applications are to be grouped in a single bundle unit;

a move together rule indicating that at least two applications are to be migrated in a single migration wave; and a sequencing rule indicating that a first application is to be migrated prior to beginning migration of a second application; and wherein the precedence flag indicates that the at least one individual data migration rule or scheduling consideration must be implemented in a migration schedule over another data migration rule or scheduling consideration;

instructions to compare the set of data migration rules against the set of scheduling considerations;

instructions to determine that a conflict exists between the set of migration rules and the set of scheduling considerations based on the comparison, instructions to select at least a first data migration rule corresponding to the precedence flag to implement over a scheduling consideration based on the determination that the conflict exists;

instructions to group applications on the source data storage in a bundle unit according to the bundling rule and at least the first data migration rule while ignoring the scheduling consideration; and instructions to generate a migration schedule for migrating the grouped applications in the bundle unit according to the move together rule, the sequencing rule, and at least the first data migration rule while ignoring the scheduling consideration.

18. The non-transitory computer readable memory of claim 17, further including instructions executable by the processor to: generate the migration schedule to identify one or more migration activities and corresponding scheduling information for the one or more migration activities.

19. The non-transitory computer readable memory of claim 18, further including instructions executable by the processor to migrate the applications in the bundle unit according to the migration activities.

20. The method of claim 1 wherein the scheduling considerations further comprise at least one of a start time, a stop time, and client availability.

21. The method of claim 1 wherein the data migration rules further comprise previous bundling rules used in a previous data migration project.

22. The method of claim 1 further comprising:

validating, by the controller, the bundle unit and the migration schedule to determine whether the bundle unit or the migration schedule violates the data migration rules or the scheduling considerations; and presenting a flag to the client to indicate that a violation exists in response to determining that the bundle unit or the migration schedule violates the data migration rules or the scheduling considerations.

* * * * *